US009388247B2

(12) United States Patent
Reiter et al.

(10) Patent No.: US 9,388,247 B2
(45) Date of Patent: *Jul. 12, 2016

(54) ANTIBODIES AGAINST CANCER TARGET BLOCK TUMOR GROWTH, ANGIOGENESIS AND METASTATIS

(75) Inventors: Robert E. Reiter, Los Angeles, CA (US); Zev Wainberg, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 1000 days.

This patent is subject to a terminal disclaimer.

(21) Appl. No.: 12/936,189

(22) PCT Filed: Apr. 3, 2009

(86) PCT No.: PCT/US2009/039526

§ 371 (c)(1),
(2), (4) Date: Jan. 24, 2011

(87) PCT Pub. No.: WO2009/124281

PCT Pub. Date: Oct. 8, 2009

(65) Prior Publication Data

US 2011/0142838 A1     Jun. 16, 2011

Related U.S. Application Data

(60) Provisional application No. 61/042,604, filed on Apr. 4, 2008, provisional application No. 61/113,054, filed on Nov. 10, 2008.

(51) Int. Cl.
*A61K 39/395* (2006.01)
*C07K 16/30* (2006.01)
*C12N 5/12* (2006.01)
*C07K 16/28* (2006.01)
*A61K 39/00* (2006.01)

(52) U.S. Cl.
CPC .............. *C07K 16/30* (2013.01); *C07K 16/2896* (2013.01); *A61K 2039/505* (2013.01); *C07K 2317/24* (2013.01); *C07K 2317/56* (2013.01); *C07K 2317/622* (2013.01); *C07K 2317/626* (2013.01); *C07K 2317/73* (2013.01); *C07K 2317/76* (2013.01)

(58) Field of Classification Search
CPC ............ A61K 39/395; A61K 39/3955; A61K 39/39558; C07K 16/28; C07K 16/2896; C07K 16/30; C07K 16/3038; C07K 2317/70; C12N 5/12
USPC ........ 530/387.1, 387.3, 388.1, 388.22, 388.7, 530/388.73, 388.75, 388.8, 388.85; 424/130.1, 133.1, 137.1, 138.1, 141.1, 424/142.1, 143.1, 144.1, 152.1, 153.1, 424/154.1, 155.1, 156.1, 172.1, 173.1, 424/174.1
See application file for complete search history.

(56) References Cited

U.S. PATENT DOCUMENTS

| | | | |
|---|---|---|---|
| 5,750,078 A | 5/1998 | Shitara et al. | |
| 5,889,157 A | 3/1999 | Pastan et al. | |
| 6,472,368 B1 | 10/2002 | Doherty et al. | |
| 6,682,901 B2 | 1/2004 | Blaschuk et al. | |
| 7,973,139 B2 | 7/2011 | Bell et al. | |
| 8,663,635 B2 * | 3/2014 | Reiter ........................ 424/130.1 |
| 8,703,920 B2 * | 4/2014 | Reiter et al. ............... 530/387.3 |
| 2002/0146687 A1 | 10/2002 | Blaschuk et al. | |
| 2003/0190602 A1 | 10/2003 | Pressman et al. | |
| 2004/0248219 A1 | 12/2004 | Blaschuk et al. | |
| 2007/0105133 A1 | 5/2007 | Clarke et al. | |
| 2010/0119527 A1 | 5/2010 | Reiter | |
| 2010/0233170 A1 | 9/2010 | Reiter et al. | |
| 2010/0278821 A1 | 11/2010 | Reiter | |
| 2011/0086029 A1 | 4/2011 | Reiter et al. | |
| 2011/0142838 A1 | 6/2011 | Reiter et al. | |

FOREIGN PATENT DOCUMENTS

| | | |
|---|---|---|
| JP | 2002-513937 | 5/2002 |
| WO | WO 99/57565 A2 | 11/1999 |
| WO | WO 01/62206 A2 | 8/2001 |
| WO | WO 01/62206 A3 | 8/2001 |
| WO | 2004/106380 A2 | 12/2004 |
| WO | WO 2007/109347 A2 | 9/2007 |
| WO | WO 2009/124281 A2 | 10/2009 |
| WO | 2010/054377 A2 | 5/2010 |
| WO | 2010/054397 A2 | 5/2010 |

OTHER PUBLICATIONS

Kortt, A. A., et al. Protein Engineering, 10(4): 423-433, 1977.*
International Search Report mailed on Sep. 4, 2009, for International Application No. PCT/US2009/039526 filed on Apr. 3, 2009, 2 pages.
Kim, J-B. et al., "N-Cadherin Extracellular Repeat 4 Mediates Epithelial to Mesenchymal Transition and Increased Motility, " *The Journal of Cell Biology*, Dec. 11, 2000, vol. 151, No. 6, pp. 1193-1205.
Adherex.com, "Adherex Presents Final Clinical Data on ADH-1 Phase 1 Trial at ASCO Annual Meeting," located at <http://www.adherex.com/news/news_items/2005-05-16>, last accessed on Jun. 27, 2010, 2 pages.
Alexander, N.R. et al., "N-cadherin Gene Expression in Prostate Carcinoma is Modulated by Integrin-Dependent Nuclear Translocation of Twist1," Cancer Research, Apr. 1, 2006, vol. 66, No. 7, pp. 3365-3369.
Beckman, R.A. et al., "Antibody Construct in Cancer Therapy, Protein Engineering Strategies to Improve Exposure in Solid Tumors," Can., 2007, vol. 109, pp. 170-179.
Blaschuk et al., "Identification of a Cadherin Cell Adhesion Recognition Sequence," Developmental Biology, 1990, vol. 139, No. 1, pp. 227-229.
Buesa, C. et al., "DNA chip technology in brain banks: confronting a degrading world," J. Neuropathol. Exp. Neurol., 2004, vol. 63, No. 10, pp. 1003-1014, Abstract.

(Continued)

*Primary Examiner* — Alana Harris Dent
*Assistant Examiner* — Anne Holleran
(74) *Attorney, Agent, or Firm* — Riverside Law LLP

(57) ABSTRACT

The present invention provides antibodies that target the first-third domains of N-cadherein and the fourth domain of N-cadherin, for diagnosis and therapy of cancers related to N-cadherein. Methods of diagnosis and treatment utilizing these antibodies are also described.

13 Claims, 33 Drawing Sheets

(56) References Cited

OTHER PUBLICATIONS

Bussemakers, M.J.G. et al., "The role of OB-cadherin in human prostate cancer," Proceedings of the Annual Meeting of the American Association for Cancer Research, New York, NY, Mar. 1, 1998, vol. 39, Abstract No. 3405, 1 page.
Céspedes, M. V. et al., "Mouse models in oncogenesis and cancer therapy," Clin. Transls. Oncol., 2006, vol. 8, No. 5, pp. 318-329.
Dennis, C., "Off by a whisker," Nature, 2006, vol. 442, pp. 739-741.
Fujimori, K. et al., "A Modeling Analysis of Monoclonal Antibody Percolation Through Tumors: A Binding-Site Barrier," J. Nuc. Med., 1990, vol. 31, pp. 1191-1198.
Harrison, O.J. et al., "The mechanism of cell adhesion by classical cadherins: the role of domain 1," Journal of Cell Science, 2005, vol. 118, No. 4, pp. 711-721.
Hatta et al., "Cloning and Expression of cDNA Encoding a Neural Calcium-dependent Cell Adhesion Molecule: Its Identity in the Cadherin Gene Family," The Journal of Cell Biology, 1988, vol. 106, No. 3, pp. 873-881.
Jaggi, M. et al., "N-Cadherin Switching Occurs in High Gleason Grade Prostate Cancer," The Prostate, 2006, vol. 66, pp. 193-199.
Kim et al., N-Cadherin Extracellular Repeat 4 Mediates Epithelial to Mesenchymal Transition and Incerased Motility, The Journal of Cell Biology, Dec. 11, 2000, vol., 151, No. 6, pp. 1193-1205.
Meyer, S. et al., "Messenger RNA Turnover in Eukaryotes: Pathways and Enzymes," Clin. Rev. Biochem. & Molec. Biol., 2004, vol. 39, pp. 197-216.
Mialhe, A. et al., "Expression of E-. P-, N-cadherins and Catenins in Human Bladder Carcinoma Cell Lines," J. Urol., Sep. 2000, vol. 164 (3 Pt 1), pp. 826-835, Abstract Only.
Price, J.T. et al., "Mechanisms of Tumor Invasion and Metastasis: Emerging Targets for Therapy," Expert Opin. Ther. Targets, 2002, vol. 6, No. 2, pp. 217-233.
Rieger-Christ, Kimberly M. et al., "Novel expression of N-cadherin elicits in vitro bladder cell invasion via the Akt signaling pathway," Oncogene, 2004, vol. 23, pp. 4745-4753.
Rudnick, S.I. et al., "Affinity and Avidity in Antibody-Based Tumor Targeting," Can. Biotherp. and Radiopharm., 2009, vol. 24, pp. 155-162.
Takeichi et al., "Cadherins: A Molecular Family Important in Selective Cell-Cell Adhesion," Annual Review of Biochemistry, 1990, vol. 59, No. 1, pp. 237-252.
Tanaka et al., "Monoclonal antibody targeting of N-cadherin inhibits prostate cancer growth, metastasis and castration resistance," Nature Medicine, 2010, vol. 16, No. 12, pp. 1414-1420.
Talmadge, J.E. et al., "Murine Models to Evaluate Novel and Conventional Therapeutic Strategies for Cancer," Am. J. Pathol., 2007, vol. 170, No. 3, pp. 793-804.
Thurber, G.M. et al., "Antibody tumor penetration: Transport opposed by systemic and antigen-mediated clearance," Adv. Drug Deliv. Rev., 2008, vol. 60, pp. 1421-1434.
Tomita, K. et al., "Cadherin Switching in Human Prostate Cancer Progression," Cancer Research, Jul. 1, 2000, vol. 60, pp. 3650-3654.
Tran, N.L. et al., "N-Cadherin Expression in Human Prostate Carcinoma Cell Lines," American Journal of Pathology, Sep. 1999, vol. 155, No. 3, pp. 787-798.
Voskoglou-Nomikos, T., "Clinical Predictive Value of the in vitro Cell Line, Human Xenograft, and Mouse Allograft Preclinical Cancer Models," Clin. Can. Res., 2003, vol. 9, pp. 4227-4239.
Wallerand, H. et al., "P-AKT Pathway Activation and Inhibition Depends on N-Cadherin or P-EGFR Expression in Invasive Human Bladder Cancer Cell Lines," Journal of Urology & Annual Meeting of the American-Urological-Association, San Antonion, TX, May 21-26, 2005, Abstract No. 582, 1 page.
Wallerland et al., "Phospho-Akt pathway activation and inhibition depends on N-cadherin or phospho-EFGR expression in invasive human bladder cancer cell lines," Urologic Oncology, 2010, vol. 28, No. 2, pp. 180-188.
Williams et al., "Identification of an N-cadherin Motif That Can Interact with the Fibroblast Growth Factor Receptor and Is Required for Axonal Growth," The Journal of Biological Chemistry, 2001, vol. 276, No. 47, pp. 43879-43886.
Sheets et al., "Efficient construction of a large nonimmune phage antibody library: The production of high-affinity human single-chain antibodies to protein antigens," Proceeding of the National Academy of Sciences, National Academy of Sciences, US, 1998, vol. 95, No. 11, pp. 6157-6162.

\* cited by examiner

ANTIBODIES AGAINST CANCER TARGET BLOCK TUMOR GROWTH, ANGIOGENESIS AND METASTATIS

CROSS-REFERENCES TO RELATED APPLICATIONS

The present application claims priority to U.S. patent application No. 61/042,604, filed Apr. 4, 2008, and U.S. patent application No. 61/113,053, filed Nov. 10, 2008, the contents of which are herein incorporated by reference in their entirety.

STATEMENT AS TO RIGHTS TO INVENTIONS MADE UNDER FEDERALLY SPONSORED RESEARCH OR DEVELOPMENT

BACKGROUND OF THE INVENTION

Prostate cancer is the most common malignancy and the second leading cause of cancer-related death in American men. Prostate cancer is a biologically and clinically heterogeneous disease. A majority of men with this malignancy harbor slow-growing tumors that may not impact an individual's natural lifespan, while others are struck by rapidly progressive, metastatic tumors. PSA screening is limited by a lack of specificity and an inability to predict which patients are at risk to develop hormone refractory metastatic disease. Recent studies advocating a lower PSA threshold for diagnosis may increase the number of prostate cancer diagnoses and further complicate the identification of patients with indolent vs. aggressive cancers (Punglia et al., *N Engl J Med*, 349: 335-342 (2003)). New serum and tissue markers that correlate with clinical outcome or identify patients with potentially aggressive disease are urgently needed (Welsh et al., *Proc Natl Acad Sci USA*, 100: 3410-3415 (2003)).

Recent expression profiling studies suggest that expression signatures for metastatic vs. non-metastatic tumors may reside in the primary tumor (Ramaswamy et al., *Nat Genet*, 33: 49-54 (2003); Sotiriou et al., *Proc Natl Acad Sci USA*, 100: 10393-10398 (2003)). Additional features that predispose tumors to metastasize to specific organs may also be present at some frequency in the primary tumor (Kang et al., *Cancer Cell*, 3: 537-549 (2003)). These recent observations suggest that novel markers of pre-metastatic or pre-hormone refractory prostate cancer may be identified in early stage disease. These markers may also play a role in the biology of metastatic or hormone refractory prostate cancer progression. Recent examples of genes present in primary tumors that correlate with outcome and play a role in the biology of prostate cancer progression include EZH2 and LIM kinase (Varambally et al., *Nature*, 419: 624-629 (2002); Yoshioka et al., *Proc Natl Acad Sci USA*, 100: 7247-7252 (2003)). However, neither of these two genes is secreted.

In order to identify new candidate serum or tissue markers of hormone refractory prostate cancer, we compared gene expression profiles of paired hormone dependent and hormone refractory prostate cancer xenografts. The LAPC-9 xenograft was established from an osteoblastic bone metastasis and progresses from androgen dependence to independence following castration in immune deficient mice (Craft et al., *Cancer Research*, In Press (1999)). It has been used previously to identify candidate therapeutic targets in prostate cancer. Differentially expressed genes were validated and then examined for sequence homology to secreted or cell surface proteins. The identification, characterization and initial validation of N-Cadherin, which is expressed in both hormone refractory prostate cancer and bladder cancer, has been previously reported (WO/2007/109347).

We previously disclosed our identification of N-cadherin as a putative diagnostic and therapeutic target in prostate and bladder cancers (WO/2007/109347). Our previous disclosure demonstrated significant expression of the target in high risk and advanced prostate and bladder tumors and showed that expression of the target is associated with poor prognosis and progression to androgen independence. Although there has been previous speculation that N-cadherin might be a useful therapy target, the only existing drug was a peptide antagonist, which did not show any preclinical activity against prostate cancer. To our knowledge, our invention provides the first monoclonal antibodies that are active against cancers expressing the target. In addition, the exisiting N-cadherin antagonist targets only the first extracellular domain of the protein. We describe antibodies that target the first and fourth extracellular domains. All have significant antitumor activity. To our knowledge, this is the first description of the concept of targeting the fourth extracellular domain. Our antibodies can be used a single agents, in combination, and also conceptually as agents that can be combined with antagonists of parallel or downstream pathways to N-cadherin.

The invention encompasses multiple monoclonal antibodies against the first and fourth extracellular domains of the N-cadherin protein. These antibodies block tumor growth, angiogenesis and metastasis in in vivo models of prostate and other cancers. They work by blocking N-cadherin signal transduction pathways that are critical for tumor growth, invasion, angiogenesis and metastasis. The antibodies may also be useful for in vivo maging of N-cadherin positive tumors and/or for tissue diagnosis and prognosis.

The invention can be practiced alone as single antibodies to treat or prevent tumor growth and metastasis. They may be used as adjuvants or as therapeutics for existing tumors. They may be used in combination to block multiple domains of the N-cadherin protein. They may also be used in combination with chemotherapy or other targeted cancer agents, particularly those that target synergistic signal transduction pathways or those that target downstream or upstream pathways involved in N-cadherin mediated signal transduction.

There are currently no approved therapes or diagnostics targeting N-cadherin. The only drug targeting this pathways has not been highly successful in Phase II trials and has shown no activity in the preclinical models that our invention is active against, suggesting the clear superiority of our approach and our agents.

Accordingly, the invention provides compositions and methods that target N-Cadherin in the diagnosis, prognosis, and treatment of cancers expressing N-Cadherin including, but not limited to, prostate cancer and bladder cancer.

BRIEF SUMMARY OF THE INVENTION

In one aspect, the present invention provides a hybridoma cell line deposited as ATCC Accession No. PTA-9387 and an antibody produced by this hybridoma cell line, as well as another hybridoma cell line deposited as ATCC Accession No. PTA-9388 and an antibody produced by this hybridoma cell line. Also provided is an antibody or fragment thereof capable of binding to domains 1-3 of N-cadherin, the same antigenic determinant of N-cadherin, in vivo or in vitro, as does the monoclonal antibody produced by the hybridoma cell line deposited at the American Type Culture Collection having ATCC Accession No. PTA-9387, or an antibody or fragment thereof capable of binding to domain 4 of N-cadherin, the same antigenic determinant of N-cadherin, in vivo or in vitro, as does the monoclonal antibody produced by the hybridoma cell line deposited at the American Type Culture Collection having ATCC Accession No. PTA-9388. Such an antibody may be humanized or fully human; or it may be a diabody or single chain antibody (scFv).

In a second aspect, this invention provides a method of inhibiting the growth of cancer cells in a patient. The method comprises the step of: administering an antibody (or its fragment) of this invention to a patient under conditions sufficient for binding the antibody (or its fragment) to the cancer cells, which express or overexpress N-Cadherin. The antibody (or its fragment) inhibits the growth of cancer cells by (a) activating or inhibiting NF kappa-β signaling and transcription; (b) activating or inhibiting N-cadherin internalization; (c) activating or inhibiting PI3 kinase or Akt pathway; (d) activating or inhibiting β-catenin signaling; (e) blocking heterodimerization of N-cadherin with FGFR or other tyrosine kinase receptor; or (f) blocking or enhancing cleavage by ADAM10 or other metallopeptidase. In some embodiments, the cancer cells are urogenital cancer cells, prostate cancer cells, or baldder cancer cells.

In a third aspect, the invention provides a method of treating a cancer patient. The method comprises the steps of: (a) obtaining a test tissue sample from an individual at risk of having a cancer that expresses a N-cadherin protein; (b) determining the presence or absence or amount of the N-cadherin protein in the test tissue sample in comparison to a control tissue sample from an individual known to be negative for the cancer; thereby diagnosing said cancer that expresses a N-cadherin protein, wherein the N-cadherin protein is expressed at normal or low levels, or is expressed by a subset of cells, or is overexpressed; and (c) administering an effective amount of N-cadherin antibody (or its fragment) of this invention to the individual at risk of having a cancer that expresses a N-Cadherin protein.

In some embodiments, the tissue sample is prostate or bladder tissue. In some embodiments, the cancer is a prostate cancer or bladder cancer, or it may be a metastatic cancer. In some embodiments, the antibody (or its fragment) blocks hormone refractory prostate cancer, or antibody blocks cancer stem cells. The antibody in some cases is a monoclonal antibody, an scFv, or a diabody. In other some embodiments, the tissue sample is prostate or bladder tissue.

In a fourth aspect, the present invention provides a method of diagnosing a cancer patient. The method comprises the steps of: (a) obtaining a test tissue sample from an individual at risk of having a cancer that expresses a N-cadherin protein; (b) determining the presence or absence or amount of the N-cadherin protein in the test tissue sample in comparison to a control tissue sample from an individual known to be negative for the cancer by contacting a sample with an effective amount of N-cadherin antibody (or its fragment) of this invention; thereby diagnosing said cancer that expresses a N-cadherin protein, wherein the N-cadherin protein is expressed at normal or low levels, or is expressed by a subset of cells, or is overexpressed.

In a fifth aspect, the present invention provides a method of identifying cancer stem cells. The method comprises the steps of: (a) obtaining a test tissue sample from an individual at risk of having a cancer that expresses a N-cadherin protein; (b) determining the presence or absence of cancer stem cells in the test tissue sample in comparison to a control tissue sample from an individual known to be negative for the cancer; wherein the N-cadherin protein is expressed at normal or low levels, or is expressed by a subset of the stem cells and is not overexpressed, using the antibody (or its fragment) of this invention. In some embodiments, the tissue sample is prostate or bladder tissue. In some embodiments, the cancer is a prostate cancer, a bladder cancer, a hormone refractory prostate cancer, or a metastatic cancer.

In a sixth aspect, the invention provides a method of identifying an anti-N-cadherin antibody or a compound that inhibits the growth of cancer cells in a patient. The method comprises the steps of: (i) contacting the candidate compound or antibody with a cell expressing or overexpressing an N-cadherin polypeptide; and (ii) determining the functional effect of the candicate compound or antibody upon the N-cadherin polypeptide by determining if the compound or antibody: (a) activates or inhibits NF kappa-β signaling and transcription; (b) activates or inhibits N-cadherin internalization; (c) activates or inhibits PI3 kinase or Akt pathway; (d) activates or inhibits β-catenin signaling; (e) blocks heterodimerization of N-cadherin with FGFR or other tyrosine kinase receptor; or (f) blocks or enhances cleavage by ADAM10 or other metallopeptidase. If the candidate compound or antibody is shown to exhibit activity in either one of (a)-(f), the antibody or compound is deemed an anti-N-Cadherin antibody or a compound that inhibits growth of N-Cadherin expressing cancers in a patient. For example, the antibody or compound is deemed an anti-N-Cadherin antibody or a compound that inhibits growth of N-Cadherin expressing cancers in a patient when the antibody or compound inhibits NF kappa-β signaling or transcription; or when the antibody or compound inhibits N-cadherin internalization.

DETAILED DESCRIPTION OF THE INVENTION

This invention relates to novel monoclonal antibodies targeting the cell surface protein N-Cadherin for therapy of cancers that express N-Cadherin. The cancers can be prostate cancer, bladder cancer, or other cancers that express N-Cadherin.

Figure 1:
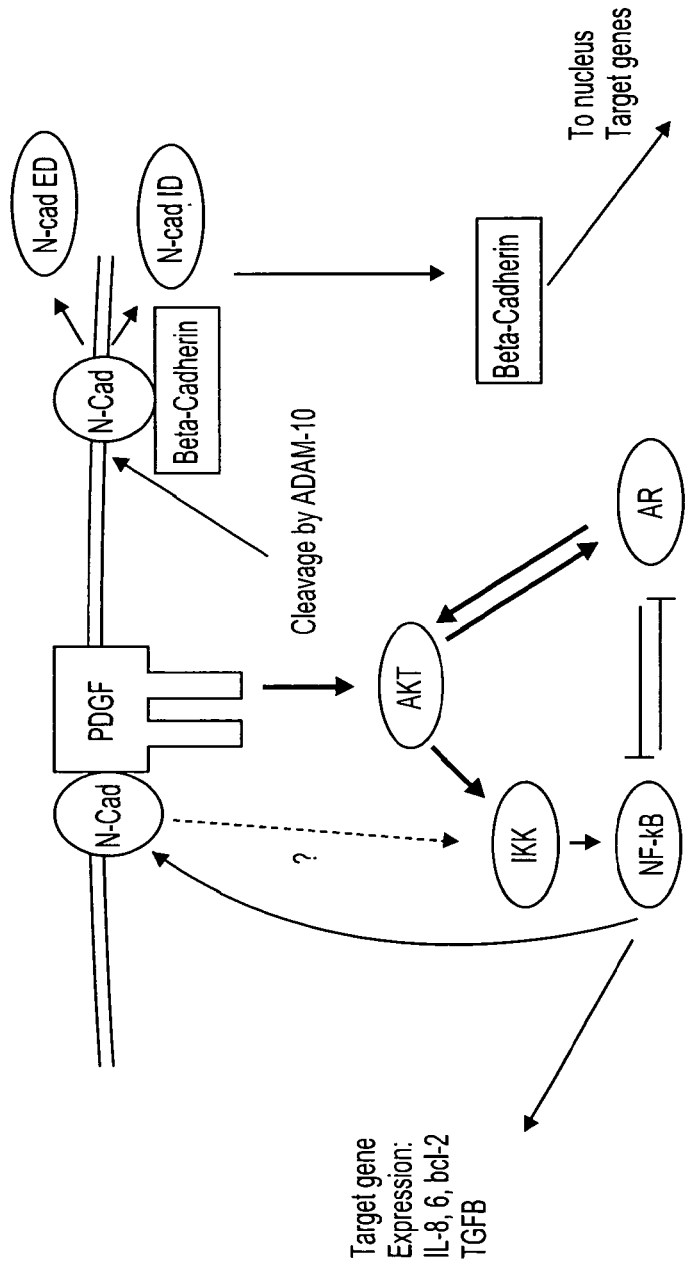
FIG. 1. Model of N-Cadherin signaling in prostate cancer.

This invention also relates to methods of treating cancers using antibodies targeting N-Cadherin. The inventors have discovered that the antibodies may work by activating or inhibiting NF kappa-β signaling and transcription, or by activating or inhibiting N-cadherin internalization, or by activating or inhibiting PI3 kinase or Akt pathway, or by activating or inhibiting β-catenin signaling, or by blocking heterodimerization of N-cadherin with FGFR or other tyrosine kinase receptor; or by blocking or enhancing cleavage by ADAM10 or other metallopeptidase. FIG. 1 is a summary of N-Cadherin mediated signal transduction. FIG. 1 shows the activation of NF-kappa β, Akt, and β-catenin pathways. The inventors report evidence showing that N-Cadherin antibodies function by altering one or more of these pathways.

Definitions

"N-Cadherin and E-Cadherin" refer to nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a respectively referenced nucleic acid or an amino acid sequence described herein, for example, as depicted in GenBank Accession Nos. NM_001792 (N-Cadherin mRNA), NP_001783 (N-Cadherin protein), NM_004360 (E-Cadherin mRNA), and NP_004351 (E-Cadherin protein); (2) specifically bind to antibodies, e.g., polyclonal antibodies, raised against an immunogen comprising a referenced amino acid sequence as depicted in GenBank Accession No. NP_001783 (N-Cadherin protein) or NP_004351 (E-Cadherin protein); immunogenic fragments respectively thereof, and conservatively modified variants respectively thereof; (3) specifically hybridize under stringent hybridization conditions to a nucleic acid encoding a referenced amino acid sequence as depicted in GenBank Accession No. NP_001783 (N-Cadherin protein) or NP_004351 (E-Cadherin protein), respectively, and conservatively modified variants respectively thereof; (4) have a nucleic acid sequence that has greater than about 95%, preferably greater than about 96%, 97%, 98%, 99%, or higher nucleotide sequence identity, preferably over a region of at least about 25, 50, 100, 150, 200, 250, 500, 1000, or more nucleotides, to a reference nucleic acid sequence as shown in GenBank Accession No. NM_001792 (N-Cadherin mRNA) or NM_004360 (E-Cadherin mRNA). A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules.

"Cancer" refers to human cancers and carcinomas, sarcomas, adenocarcinomas, lymphomas, leukemias, etc., including solid tumors and lymphoid cancers, kidney, breast, lung, kidney, bladder, colon, ovarian, prostate, pancreas, stomach, brain, head and neck, skin, uterine, testicular, esophagus, and liver cancer, lymphoma, including non-Hodgkin's and Hodgkin's lymphoma, leukemia, and multiple myeloma. "Urogenital cancer" refers to human cancers of urinary tract and genital tissues, including but not limited to kidney, bladder, urinary tract, urethra, prostrate, penis, testicle, vulva, vagina, cervical and ovary tissues.

The cancer to be treated herein may be one characterized by excessive activation of N-cadherin. Alternatively, the cancer to be treated herein may be one where the N-cadherin protein is expressed at normal or low levels, or one where the N-cadherin protein is expressed by a subset of cells, and where the N-cadherin protein is not overexpressed. In one embodiment of the invention, a diagnostic or prognostic assay will be performed to determine whether the patient's cancer is characterized by expression of N-cadherin. Various assays for determining such amplification/expression are contemplated and include the immunohistochemistry, FISH and shed antigen assays, southern blotting, or PCR techniques. Moreover, the N-cadherin expression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label. In some embodiments, the cancer to be treated is not yet invasive, but expresses N-cadherin.

"Therapy resistant" cancers, tumor cells, and tumors refers to cancers that have become resistant or refractory to either or both apoptosis-mediated (e.g., through death receptor cell signaling, for example, Fas ligand receptor, TRAIL receptors, TNF-R1, chemotherapeutic drugs, radiation) and non-apoptosis mediated (e.g., toxic drugs, chemicals) cancer therapies, including chemotherapy, hormonal therapy, radiotherapy, and immunotherapy.

"Overexpression" refers to RNA or protein expression of N-Cadherin, LY6-E, and E-Cadherin in a test tissue sample that is significantly higher that RNA or protein expression of N-Cadherin, LY6-E, and E-Cadherin, respectively, in a control tissue sample. In one embodiment, the tissue sample is autologous. Cancerous test tissue samples (e.g., bladder, prostate) associated with invasiveness, metastasis, hormone independent (e.g., androgen independence), or refractoriness to treatment or an increased likelihood of same typically have at least two fold higher expression of N-Cadherin or LY6-E mRNA or protein, often up to three, four, five, eight, ten or more fold higher expression of N-Cadherin, or LY6-E in comparison to cancer tissues from patients who are less likely to progress to metastasis or to normal (i.e., non-cancer) tissue samples. Such differences may be readily apparent when viewing the bands of gels with approximately similarly loaded with test and controls samples. Prostate cancers expressing increased amounts of N-Cadherin or Ly6-E are more likely to become invasive, metastasize, or progress to androgen independent or treatment refractory cancer. Various cutoffs are pertinent for N-Cadherin or Ly6-E positivity, since it is possible that a small percentage of N-Cadherin or Ly6-E positive cells in primary tumors may identify tumors with a high risk for recurrence and metastasis. The terms "overexpress," "overexpression" or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 50%, 60%, 70%, 80%, 90% or more in comparison to a normal cell or comparison cell (e.g., a BPH cell).

The terms "cancer that expresses N-Cadherin" and "cancer associated with the expression of N-Cadherin" interchangeably refer to cancer cells or tissues that express N-Cadherin in accordance with the above definition.

The terms "cancer-associated antigen" or "tumor-specific marker" or "tumor marker" interchangeably refers to a molecule (typically protein, carbohydrate or lipid) that is preferentially expressed in a cancer cell in comparison to a normal cell, and which is useful for the preferential targeting of a pharmacological agent to the cancer cell. A marker or antigen can be expressed on the cell surface or intracellularly. Oftentimes, a cancer-associated antigen is a molecule that is expressed or stabilized with minimal degradation in a cancer cell in comparison to a normal cell, for instance, 2-fold expression, 3-fold expression or more in comparison to a normal cell. Oftentimes, a cancer-associated antigen is a molecule that is inappropriately synthesized in the cancer cell, for instance, a molecule that contains deletions, additions or mutations in comparison to the molecule expressed on a normal cell. Oftentimes, a cancer-associated antigen will be expressed exclusively in a cancer cell and not synthesized or expressed in a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal. Exemplified intracellular tumor markers include, for example, mutated tumor suppressor or cell cycle proteins, such as p53.

E-cadherin is conversely typically underexpressed in cancerous tissue samples in tissue samples from cancer patients which are likely to become invasive, metastasize, or progress to androgen independent or treatment refractory cancer. This underexpression may be two-fold, three-fold, four-fold, or at least five-fold. Such differences may be readily apparent when viewing the bands of gels with approximately similarly loaded with test and controls samples. The combined N-cadherin/E-cadherin values in cancers which are likely to become invasive, metastasize, or progress to androgen independent or treatment refractory cancer, are therefore even greater and can be at least two-fold, three-fold, four-fold, five-fold, ten-fold, or twenty-fold greater. Various cutoffs are pertinent for N-Cadherin positivity/e-cadherin negativity, since it is possible that a small percentage of N-Cadherin positive cells in primary tumors may identify tumors with a high risk for recurrence and metastasis.

An "agonist" refers to an agent that binds to a polypeptide or polynucleotide of the invention, stimulates, increases, activates, facilitates, enhances activation, sensitizes or up regulates the activity or expression of a polypeptide or polynucleotide of the invention.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, siRNA, antibody, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

Cytotoxic agents include "cell-cycle-specific" or "antimitotic" or "cytoskeletal-interacting" drugs. These terms interchangeably refer to any pharmacological agent that blocks cells in mitosis. Such agents are useful in chemotherapy. Generally, cell-cycle-specific-drugs bind to the cytoskeletal protein tubulin and block the ability of tubulin to polymerize into microtubules, resulting in the arrest of cell division at metaphase. Exemplified cell-cycle-specific drugs include vinca alkaloids, taxanes, colchicine, and podophyllotoxin. Exemplified vinca alkaloids include vinblastine, vincristine, vindesine and vinorelbine. Exemplifed taxanes include paclitaxel and docetaxel. Another example of a cytoskeletal-interacting drug includes 2-methoxyestradiol.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length.

The design and making of siRNA molecules and vectors are well known to those of ordinary skill in the art. For instance, an efficient process for designing a suitable siRNA is to start at the AUG start codon of the mRNA transcript (e.g., see, FIG. 5) and scan for AA dinucleotide sequences (see, Elbashir et al. EMBO J 20: 6877-6888 (2001). Each AA and the 3' adjacent nucleotides are potential siRNA target sites. The length of the adjacent site sequence will determine the length of the siRNA. For instance, 19 adjacent sites would give a 21 Nucleotide long siRNA siRNAs with 3' overhanging UU dinucleotides are often the most effective. This approach is also compatible with using RNA pol III to transcribe hairpin siRNAs. RNA pol III terminates transcription at 4-6 nucleotide poly(T) tracts to create RNA molecules having a short poly(U) tail. However, siRNAs with other 3' terminal dinucleotide overhangs can also effectively induce RNAi and the sequence may be empirically selected. For selectivity, target sequences with more than 16-17 contiguous base pairs of homology to other coding sequences can be avoided by conducting a BLAST search (see, National Center for Biotechnology Information (NCBI) website: ncbi.nlm.nih.gov/BLAST).

The siRNA can be administered directly or an siRNA expression vectors can be used to induce RNAi can have different design criteria. A vector can have inserted two inverted repeats separated by a short spacer sequence and ending with a string of T's which serve to terminate transcription. The expressed RNA transcript is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary. A preferred order of the siRNA expression cassette is sense strand, short spacer, and antisense strand. Hairpin siRNAs with these various stem lengths (e.g., 15 to 30) can be suitable. The length of the loops linking sense and antisense strands of the hairpin siRNA can have varying lengths (e.g., 3 to 9 nucleotides, or longer). The vectors may contain promoters and expression enhancers or other regulatory elements which are operably linked to the nucleotide sequence encoding the siRNA. The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. These control elements may be designed to allow the clinician to turn off or on the expression of the gene by adding or controlling external factors to which the regulatory elements are responsive.

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Determining the functional effect" refers to assaying for a compound that increases or decreases a parameter that is indirectly or directly under the influence of a polynucleotide or polypeptide of the invention, e.g., measuring physical and chemical or phenotypic effects. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; measurement of calcium influx; measurement of the accumulation of an enzymatic product of a polypeptide of the invention or depletion of an substrate; changes in enzymatic activity, e.g., kinase activity, measurement of changes in protein levels of a polypeptide of the invention; measurement of RNA stability; G-protein binding; G-protein coupled receptor (GPCR) phosphorylation or dephosphorylation; signal transduction, e.g., receptor-ligand interactions, second messenger concentrations (e.g., cAMP, IP3, or intracellular $Ca^{2+}$); identification of downstream or reporter gene expression (CAT, luciferase, β-gal, GFP and the like), e.g., via chemiluminescence, fluorescence, colorimetric reactions, antibody binding, inducible markers, and ligand binding assays.

Samples or assays comprising a nucleic acid or protein disclosed herein that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition is achieved when the activity value relative to the control is about 80%, preferably 50%, more preferably 25-0%. Activation is achieved when the activity value relative to the control (untreated with activators) is 110%, more preferably 150%, more preferably 200-500% (i.e., two to five fold higher relative to the control), more preferably 1000-3000% higher.

"Biological sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (i.e., prostate, lymph node, liver, bone marrow, blood cell), the size and type of the tumor (i.e., solid or suspended (i.e., blood or ascites)), among other factors. Representative biopsy techniques include excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine,* Kasper, et al., eds., 16th ed., 2005, Chapter 70, and throughout Part V.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%,94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI website: ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (NCBI) website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when:

the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$, is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current*

*Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et at, *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein. Such effector moieties include, but are not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic agent.

The immunoconjugate can be used for targeting the effector moiety to a N-cadherin positive cell, particularly cells, which express the N-cadherin or Ly6 protein. Such differences can be readily apparent when viewing the bands of gels with approximately similarly loaded with test and controls samples. Examples of cytotoxic agents include, but are not limited to ricin, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme.

In some embodiments, the invention provides antibodies to N-cadherin. N-cadherin antibodies may be used systemically to treat cancer (e.g., prostate or bladder cancer) alone or when conjugated with an effector moiety. N-cadherin antibodies conjugated with toxic agents, such as ricin, as well as unconjugated antibodies may be useful therapeutic agents naturally targeted to N-cadherin -bearing prostate cancer cells. Such antibodies can be useful in blocking invasiveness. Suitable N-cadherin antibodies for use according to the invention include, but are not limited to, GC4, 1H7, 1F12, and 2B3.

Additionally, the recombinant protein of the invention comprising the antigen-binding region of any of the monoclonal antibodies of the invention can be used to treat cancer. In such a situation, the antigen-binding region of the recombinant protein is joined to at least a functionally active portion of a second protein having therapeutic activity. The second protein can include, but is not limited to, an enzyme, lymphokine, oncostatin or toxin. Suitable toxins include doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, ricin, abrin, glucocorticoid and radioisotopes.

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery"in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

By "therapeutically effective dose or amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

Epithelial to Mesenchymal Transition (EMT) refers to the acquisition of stromal features by epithelial tumor cells. In cancer, EMT is associated with invasive and motile behavior and may be central process underlying metastasis. EMT is asssociated with poor prognosis and is mediated by multiple transcription factors, such as, SNAIL, SLUG and TWIST.

E-Cadherin is a cell surface protein that is involved in epithelial cell-cell adhesion and is commonly lost in invasive and metastatic solid tumors.

Detailed Embodiments

The present invention discloses two mouse hybridoma cell lines that produces monoclonal antibody capable of binding to the antigenic determinant of N-cadherin. The mouse hybridoma cell lines are deposited as ATCC Accession No. PTA-9387 (1H7) and ATCC Accession No. PTA-9388 (EC4).

In one embodiment of the invention, an antibody is produced by the hybridoma cell line designated as ATCC Accession No. PTA-9387. In another embodiment of the invention, an antibody is produced by the hybridoma cell line designated as ATCC Accession No. PTA-9388.

The cells were deposited as ATCC Accession No. PTA-9387 and ATCC Accession No. PTA-9388 pursuant to the Budapest Treaty at the American Type Culture Collection (ATCC), 10801 University Boulevard, Manassas, Va. 20110, on Jul. 23, 2008. Viability was tested and certified on Aug. 29, 2008.

The ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR §1.14 and 35 U.S.C. §122 . the deposited material will be maintained with all the care necessary to keep it viable and uncontaminated for a period of at least five years after the most recent request for the furnishing of a sample of the deposited cell line, and in any case, for a period of at least thirty (30) years after the date of deposit or for the enforceable life of the patent, whichever period is longer. The Applicants' assignee acknowledges its duty to replace the deposit should be depository be unable to furnish a sample when requested due to the condition of the deposit.

In some embodiments of the invention, an antibody or fragment thereof capable of binding to the same antigenic determinant of N-cadherin, in vivo or in vitro, as does the monoclonal antibody produced by the hybridoma cell line deposited at the American Type Culture Collection having ATCC Accession No. PTA-9387 is produced. In some embodiments of the invention, an antibody or fragment thereof capable of binding to the same antigenic determinant of N-cadherin, in vivo or in vitro, as does the monoclonal antibody produced by the hybridoma cell line deposited at the American Type Culture Collection having ATCC Accession No. PTA-9388 is produced.

In some embodiments, the antibody is capable of binding to the first extracellular domain of N-cadherin. In some embodiments, the antibody is capable of binding to the second extracellular domain of N-cadherin. In some embodiments, the antibody is capable of binding to the third extracellular domain of N-cadherin. In some embodiments, the antibody is capable of binding to the first to third extracellular domains of N-cadherin. In some embodiments, the antibody is capable of binding to the fourth extracellular domain of N-cadherin.

The present invention further relates to methods of inhibiting the growth, or killing, of cancer cells in a patient. The methods generally comprise administering the antibody or binding fragment thereof of claim 5 or 11 to a patient under conditions sufficient for binding the antibody or binding fragment thereof to said tumor cells or prostate cancer tumor cells; modulating cellular activity; inhibiting angiogenesis of the tumor cells; and causing growth inhibition or killing of the tumor cells, wherein the cancer cells express or overexpress N-Cadherin.

In some embodiments of the invention, the antibody modulates cellular activity by activating or inhibiting NF kappa-β signaling and transcription. In some embodiments of the invention, the antibody modulates cellular activity by activating or inhibiting N-cadherin internalization. In some embodiments of the invention, the antibody modulates cellular activity by activating or inhibiting PI3 kinase or Akt pathway. In some embodiments of the invention, the antibody modulates cellular activity by activating or inhibiting β-catenin signaling. In some embodiments of the invention, the antibody modulates cellular activity by blocking heterodimerization of N-cadherin with FGFR or other tyrosine kinase receptor. In some other embodiments of the invention, the antibody modulates cellular activity by blocking or enhancing cleavage by ADAM10 or other metallopeptidase.

In some embodiments, the antibody of inhibiting the growth, or killing, of urogenital cancer cells in a patient. In some embodiments, the antibody of inhibiting the growth, or killing, of prostate cancer cells in a patient. In some other embodiments, the antibody of inhibiting the growth, or killing, of baldder cancer cells in a patient.

Formulation and Administration

The anti-N-cadherin antibodies or immunoconjugates are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. The administration may be local or systemic.

The compositions for administration will commonly comprise an agent as described herein (e.g., N-cadherin inhibitors, N-cadherin antibodies and immunoconjugates, N-cadherin siRNA and vectors thereof) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration will vary according to the agent. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, of the antibodies and immunoconjugates and inhibitors for use with the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e. g. Zn-protein complexes); and/or non-ionic surfactants. The antibody can be formulated at a concentration of between 0.5-200 mg/ml, or between 10-50 mg/ml.

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly(2-hydroxyethyl-methacrylate), or poly(vinylalcohol)), polylactides. The antibodies and immunoconjugates may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as 5FU, vinblastine, actinomycin D, cisplatin, methotrexate, and the like.

In other embodiments, the methods of the invention with other cancer therapies (e.g, radical prostatectomy), radiation therapy (external beam or brachytherapy), hormone therapy (e.g., orchiectomy, LHRH-analog therapy to suppress testosterone production, anti-androgen therapy), or chemotherapy. Radical prostatectomy involves removal of the entire prostate gland plus some surrounding tissue. This treatment is used commonly when the cancer is thought not to have spread beyond the tissue. Radiation therapy is commonly used to treat prostate cancer that is still confined to the prostate gland, or has spread to nearby tissue. If the disease is more advanced, radiation may be used to reduce the size of the tumor. Hormone therapy is often used for patients whose prostate cancer has spread beyond the prostate or has recurred. The objective of hormone therapy is to lower levels of the male hormones, androgens and thereby cause the prostate cancer to shrink or grow more slowly. Luteinizing hormone-releasing hormone (LHRH) agonists decrease the production of testosterone. These agents may be injected either monthly or longer. Two such analogs are leuprolide and goserelin. Anti-androgens (e.g., flutamide, bicalutamide, and nilutamide) may also be used. Total androgen blockade refers to the use of anti-androgens in combination with orchiectomy or LHRH analogs, the s combination is called. Chemotherapy is an option for patients whose prostate cancer has spread outside of the prostate gland and for whom hormone therapy has failed. It is not expected to destroy all of the cancer cells, but it may slow tumor growth and reduce pain. Some of the chemotherapy drugs used in treating prostate cancer that has returned or continued to grow and spread after treatment with hormonal therapy include doxorubicin (Adriamycin), estramustine, etoposide, mitoxantrone, vinblastine, and paclitaxel. Two or more drugs are often given together to reduce the likelihood of the cancer cells becoming resistant to chemotherapy. Small cell carcinoma is a rare type of prostate cancer that is more likely to respond to chemotherapy than to hormonal therapy.

In some embodiments, a "cardioprotectant" is also administered with the N-cadherin antibody, N-cadherin binding inhibitor, or N-cadherin siRNA molecule for use to according to the invention (see, U.S. Pat. No. 6,949,245). A cardioprotectant is a compound or composition which prevents or reduces myocardial dysfunction (i.e. cardiomyopathy and/or congestive heart failure) associated with administration of a drug, such as an anthracycline antibiotic to a patient. The cardioprotectant may, for example, block or reduce a free-radical-mediated cardiotoxic effect and/or prevent or reduce oxidative-stress injury. Examples of cardioprotectants encompassed by the present definition include the iron-chelating agent dexrazoxane (ICRF-187) (Seifert et al. The Annals of Pharmacotherapy 28:1063-1072 (1994)); a lipid-lowering agent and/or anti-oxidant such as probucol (Singal et al. J. Mol. Cell Cardiol. 27:1055-1063 (1995)); amifostine (aminothiol 2-[(3-aminopropyl)amino]ethanethiol-dihydrogen phosphate ester, also called WR-2721, and the dephosphorylated cellular uptake form thereof called WR-1065) and S-3-(3-methylaminopropylamino)propylphosphoro-thioic acid (WR-151327), see Green et al. Cancer Research 54:738-741 (1994); digoxin (Bristow, M. R. In: Bristow M R, ed. Drug-Induced Heart Disease. New York: Elsevier 191-215 (1980)); beta-blockers such as metoprolol (Hjalmarson et al. Drugs 47:Suppl 4:31-9 (1994); and Shaddy et al. Am. Heart J. 129:197-9 (1995)); vitamin E; ascorbic acid (vitamin C); free radical scavengers such as oleanolic acid, ursolic acid and N-acetylcysteine (NAC); spin trapping compounds such as alpha-phenyl-tert-butyl nitrone (PBN); (Paracchini et al., Anticancer Res. 13:1607-1612 (1993)); selenoorganic compounds such as P251 (Elbesen); and the like.

The combined administrations contemplates coadministration, using separate formulations or a single pharmaceutical formulation, and consecutive administration in either order, wherein preferably there is a time period while both (or all) active agents simultaneously exert their biological activities.

Molecules and compounds identified that indirectly or directly modulate the expression and/or function of a N-cadherin protein can be useful in treating cancers that,respectively, express N-cadherin. N-cadherin protein modulators can be administered alone or co-administered in combination with conventional chemotherapy, radiotherapy or immunotherapy as well as currently developed therapeutics.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

Preferred pharmaceutical preparations deliver one or more active N-cadherin protein modulators, optionally in combination with one or more chemotherapeutic agents or immunotherapeutic agents, in a sustained release formulation. Typically, the N-cadherin modulator is administered therapeutically as a sensitizing agent that increases the susceptibility of tumor cells to other cytotoxic cancer therapies, including chemotherapy, radiation therapy, immunotherapy and hormonal therapy.

In therapeutic use for the treatment of cancer, the N-cadherin modulators or inhibitors utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The pharmaceutical preparations (e.g., N-cadherin siRNAs, N-cadherin antibodies, N-cadherin vaccines, N-cadherin inhibitors, and immunoconjugates) for use according to the invention are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

EXAMPLES

The following examples are offered to illustrate, but not limit the claimed invention.

Example 1

NF Kappa β Reporter Assay with TAL as Negative Control

Figure 2:
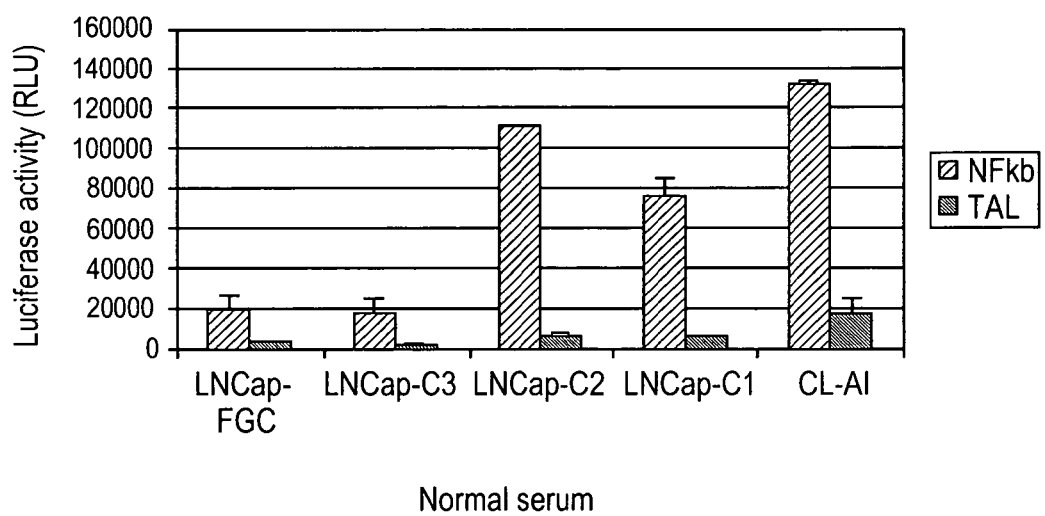
FIG. 2. N-Cadherin activates NF-γβ.
Figure 3:
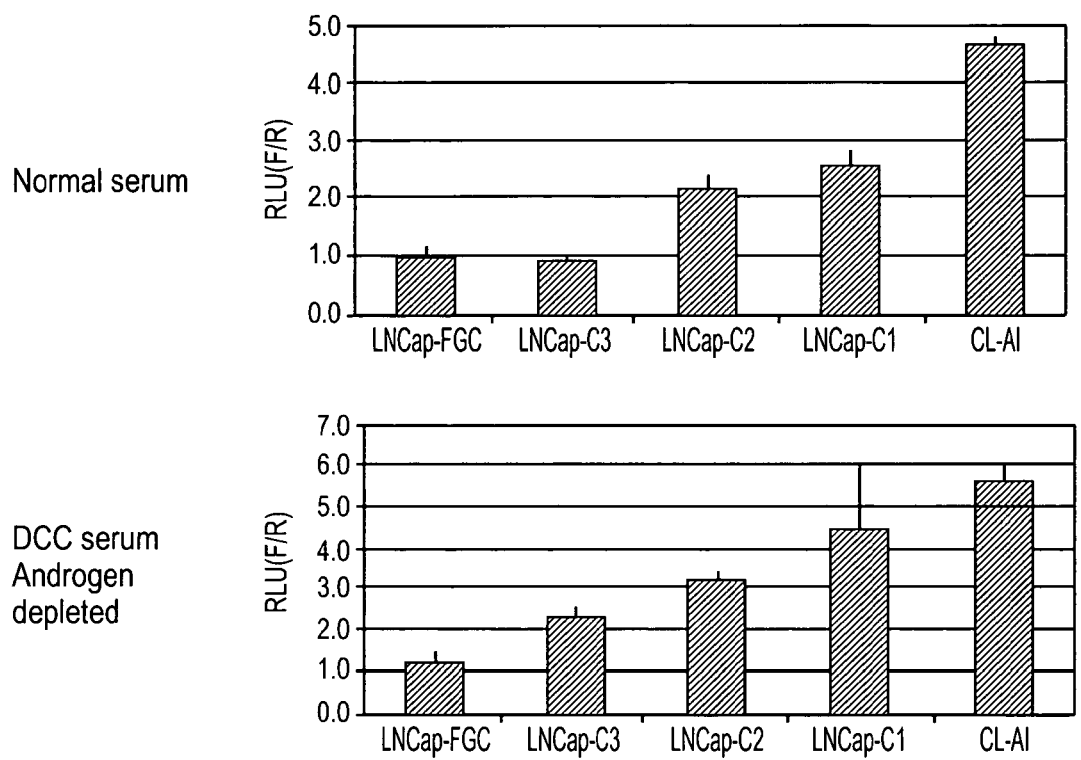
FIG. 3. N-Cadherin activates NF-γβ.

As shown in FIGS. 2-3, NF kappa β reporter activity is increased in cells that express stable N-cadherin. This is true both in androgen replete and depleted media. Also shown is that NF kappa β activation correlates with the amount of N-cadherin expression, since LNCaP-C1 expresses more N-cadherin than C2 and C3.

Example 2

Figure 4:
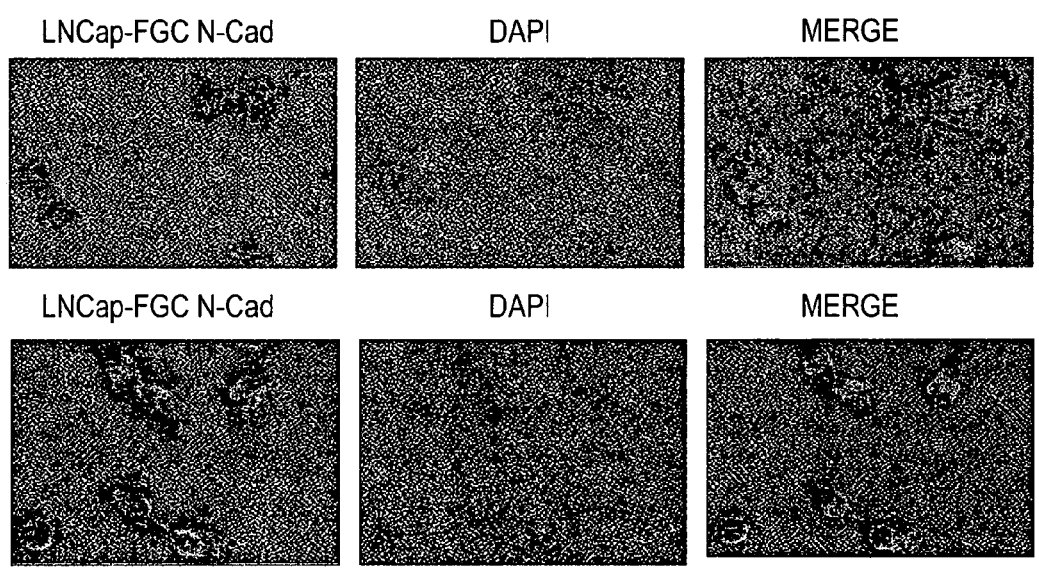
FIG. 4. N-Cadherin is expressed on cell surface of C1 cells.
Figure 5:
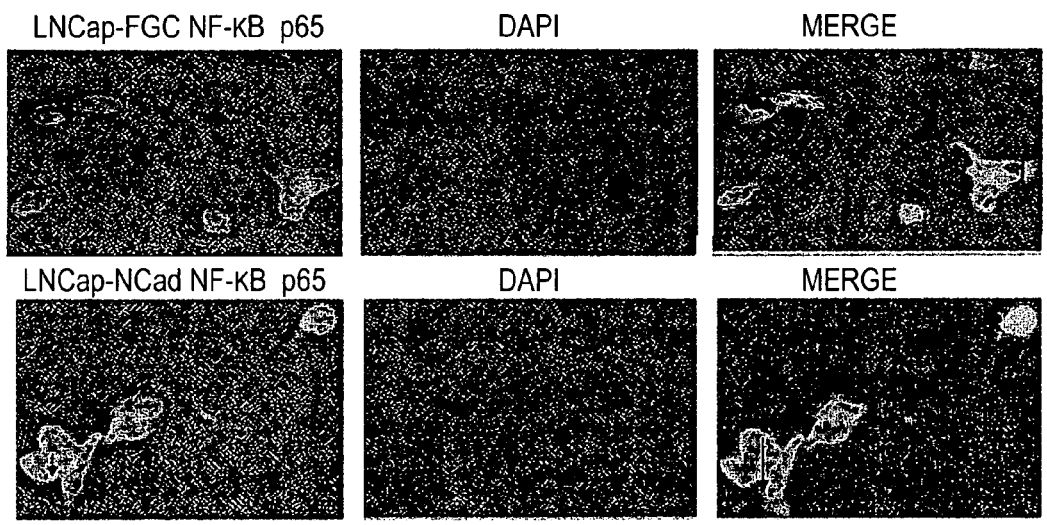
FIG. 5. NF-γβ localizes to nucleus in N-Cadherin positive cells (C1).

As shown in FIGS. 4-5, N-cadherin is expressed on the cell surface of LNCaP-C1 cells, and that these cells have both higher amounts of NF kappa β expression, but that NF kappa β is activated, as shown by the strong nuclear signal in C1 cells. Control cells also express NF kappa β, but it is localized primarily to the cytoplasm.

Example 3

Figure 6:
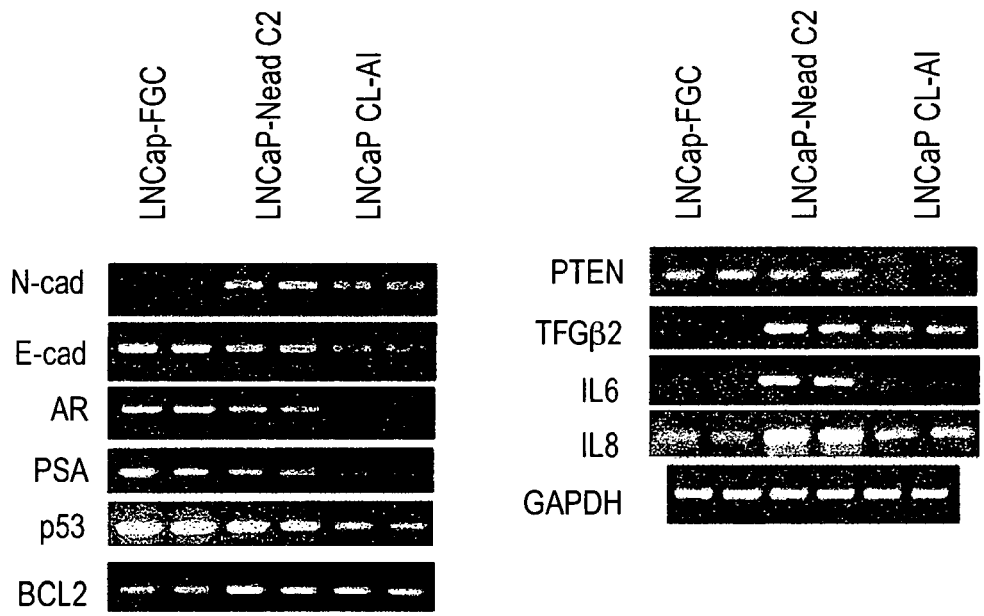
FIG. 6. N-Cadherin expression results in induction of IL-6, IL-8, TGFβ2, and bcl-2.
Figure 7:
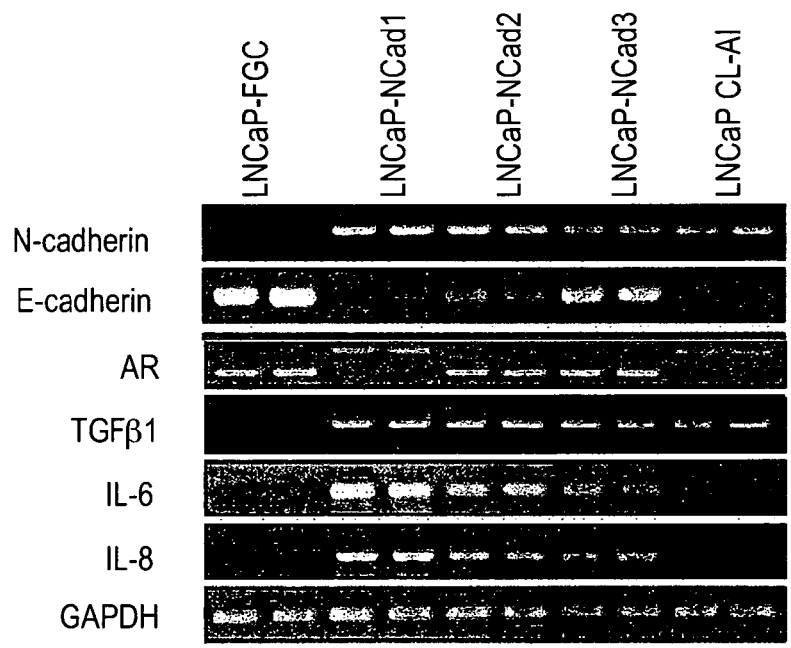
FIG. 7: Correlation of induced genes with N-Cadherin level.

FIGS. 6-7 show that NF kappa β activation by N-cadherin showing upregulation of the NF kappa β target genes TGF β, IL-6, IL-8, and bcl-2.

Example 4

Figure 8:
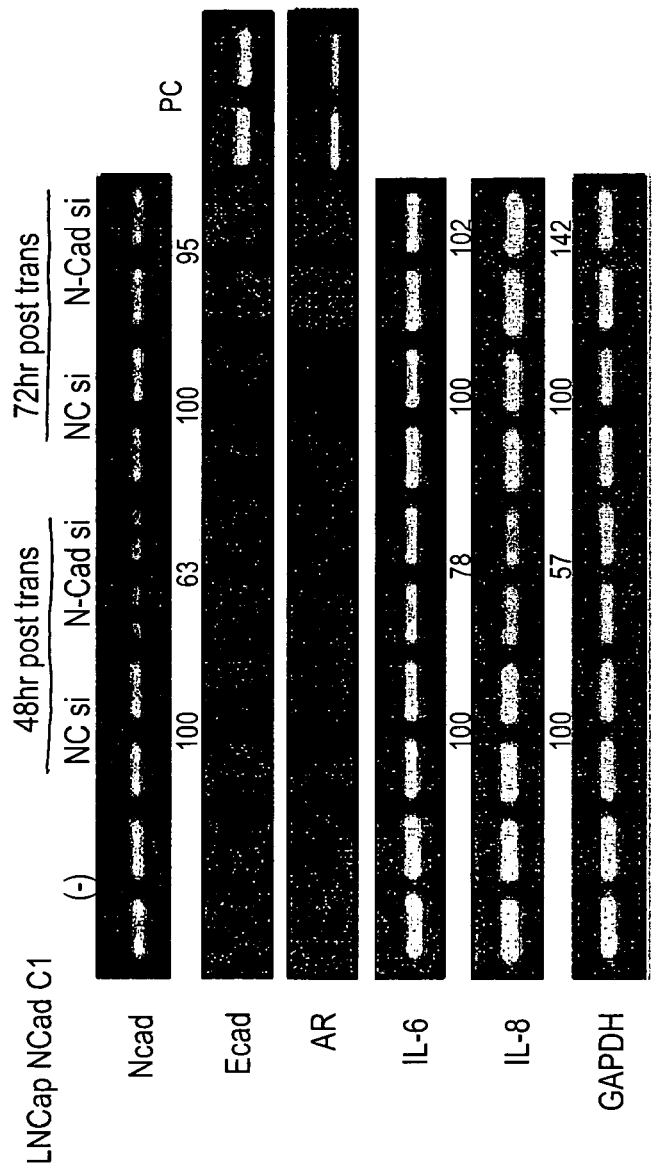
FIG. 8: N-Cadeherin knockdown leads to downregulation of IL-6 and IL-8.

As shown in FIG. 8, knockdown of N-cadherin causes reduction in NF kappa β target gene expression, such as IL-6 and IL-8, again showing that N-cadherin regulated NF kappa β.

Example 5

Figure 9:
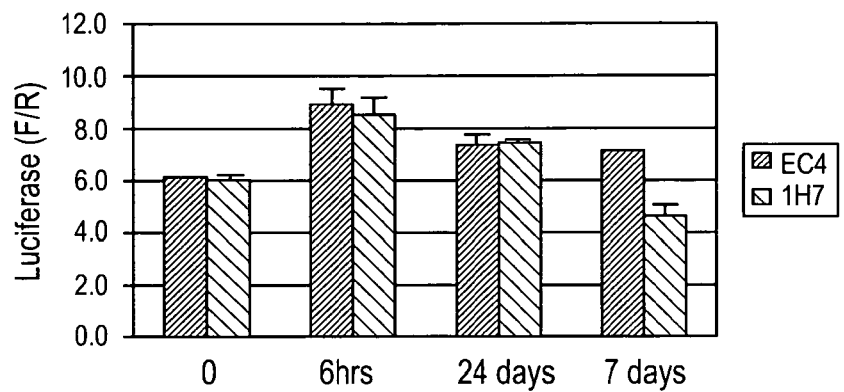
FIG. 9. NF-γβ activity after N-Cadherin antibodies treatment.

FIG. 9 shows NF kappa β promoter activity before and after treatment with N-cadherin targeted antibodies. The data show that there is immediate upregulation of NF kappa β mediated by these antibodies, which is followed at 7 days by downregulation. These data show that the antibodies may work in part by altering NF kappa β downstream signal transduction.

Example 6

Figure 10:
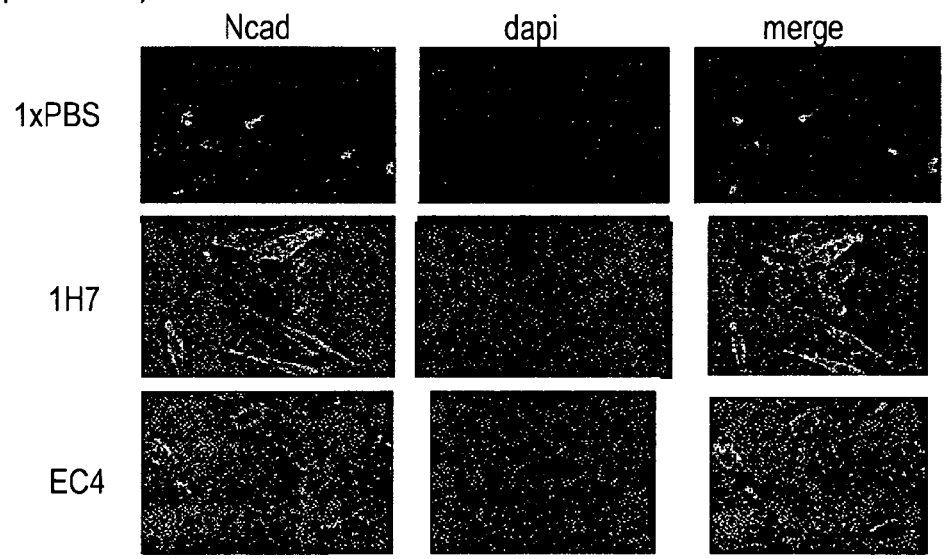
FIG. 10. N-Cadherin in PC3 cells: 48-hour antibody incubation.

FIG. 10 shows the staining of N-cadherin with and without treatment with N-cadherin targeted antibodies. In control treated cells, most N-cadherin is seen intracellularly; while in the presence of antibody, N-cadherin expression is stabilized on the cell surface. These data suggest that stabilization of N-cadherin on the cell surface is another mechanism of action of N-cadherin antibodies. This likely results in alterations in beta-catenin signaling that are mediated through cleavage and internalization of N-cadherin by metallopeptidases such as ADAM10, among others.

Example 7

Figure 11:
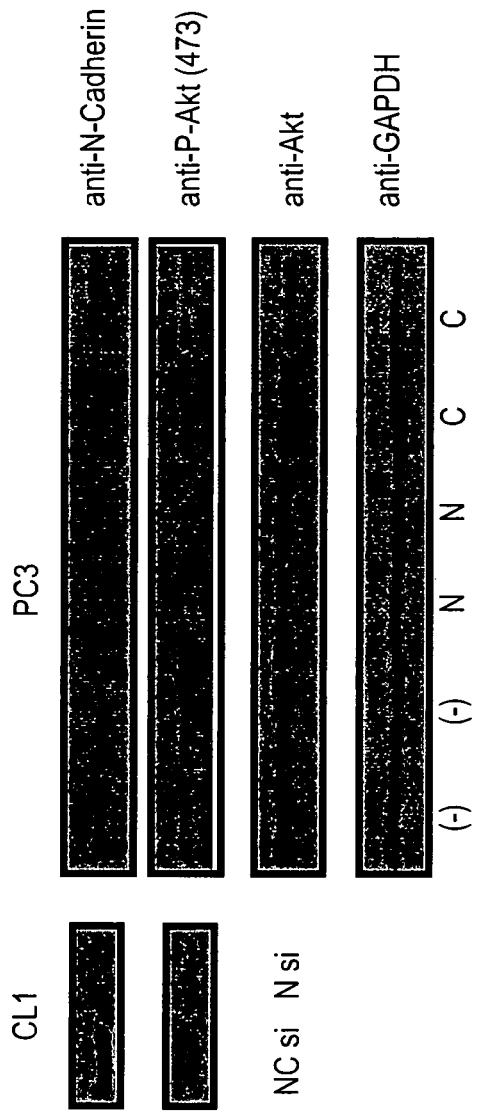
FIG. 11. N-Cadherin knockdown leads to downregulation of activated Akt.

As shown in FIG. 11, N-cadherin downregulation can cause reductions in activation of the PI3K/Akt signaling pathway.

Example 8

Figure 12:
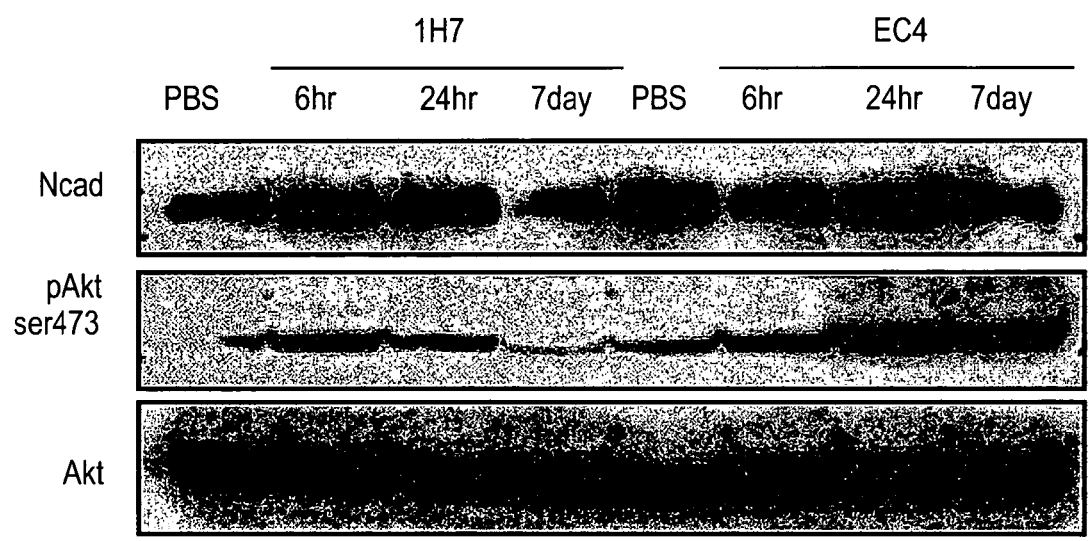
FIG. 12. N-Cadherin specific antibodies activate, then downregulate Akt activation.

As shown in FIG. 12, the treatment of cells with N-cadherin targeted antibodies causes alterations (both up and down) of Akt phosphorylation or activation, which supports the notion that these antibodies work, all or in part, by altering PI3K-Akt signal transduction.

Example 9

Figure 13:
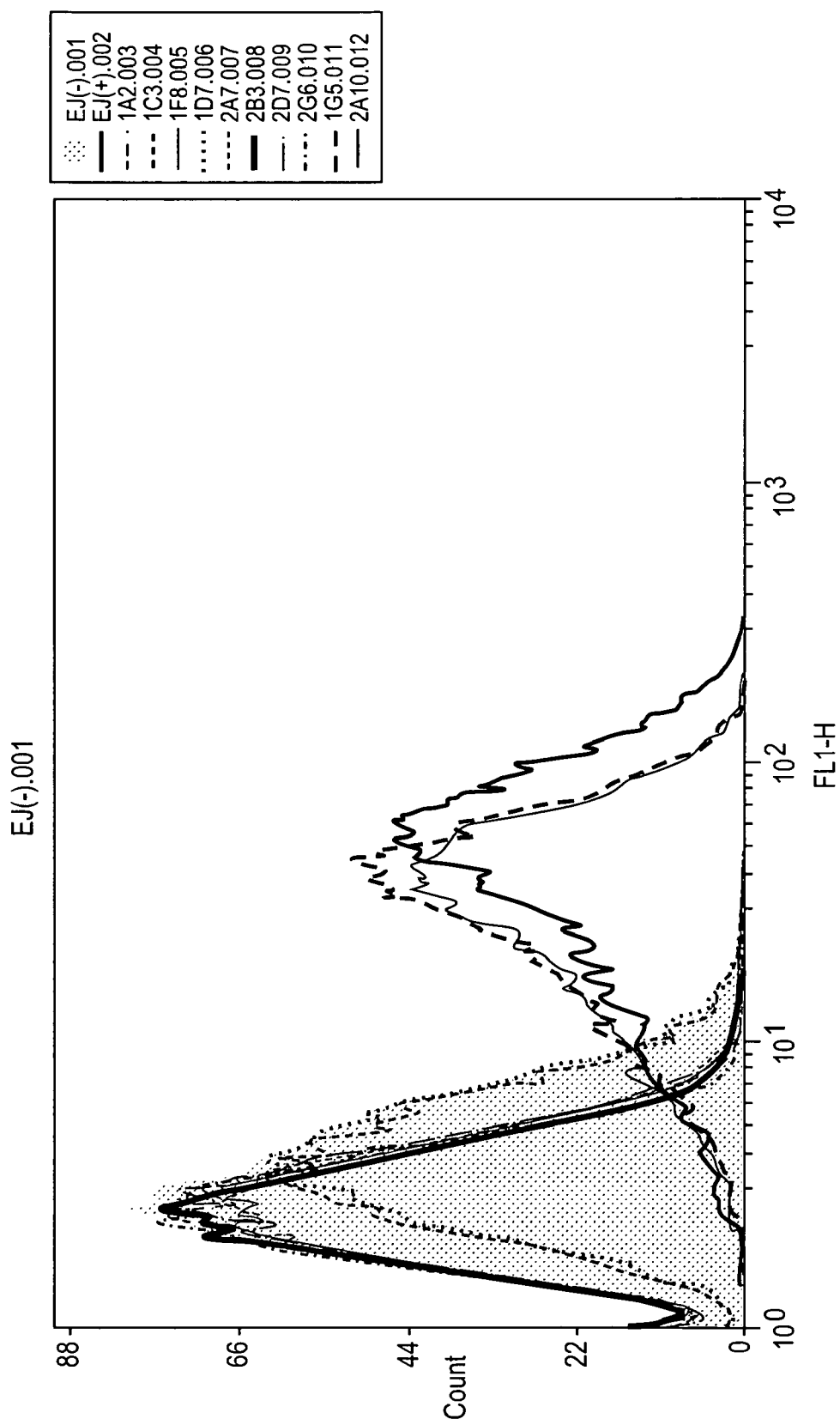
FIG. 13. FACS analysis of antibody clones targeting the first extracellular domain of the N-Cadherin protein.

FACS Analyis Showing Screening of Antibodies Clones Targeting the First Extracellular Domain of the N-Cadherin Protein FIG. 13 shows recognition of the protein on the surface of prostate cancer cells.

Example 10

Figure 14:
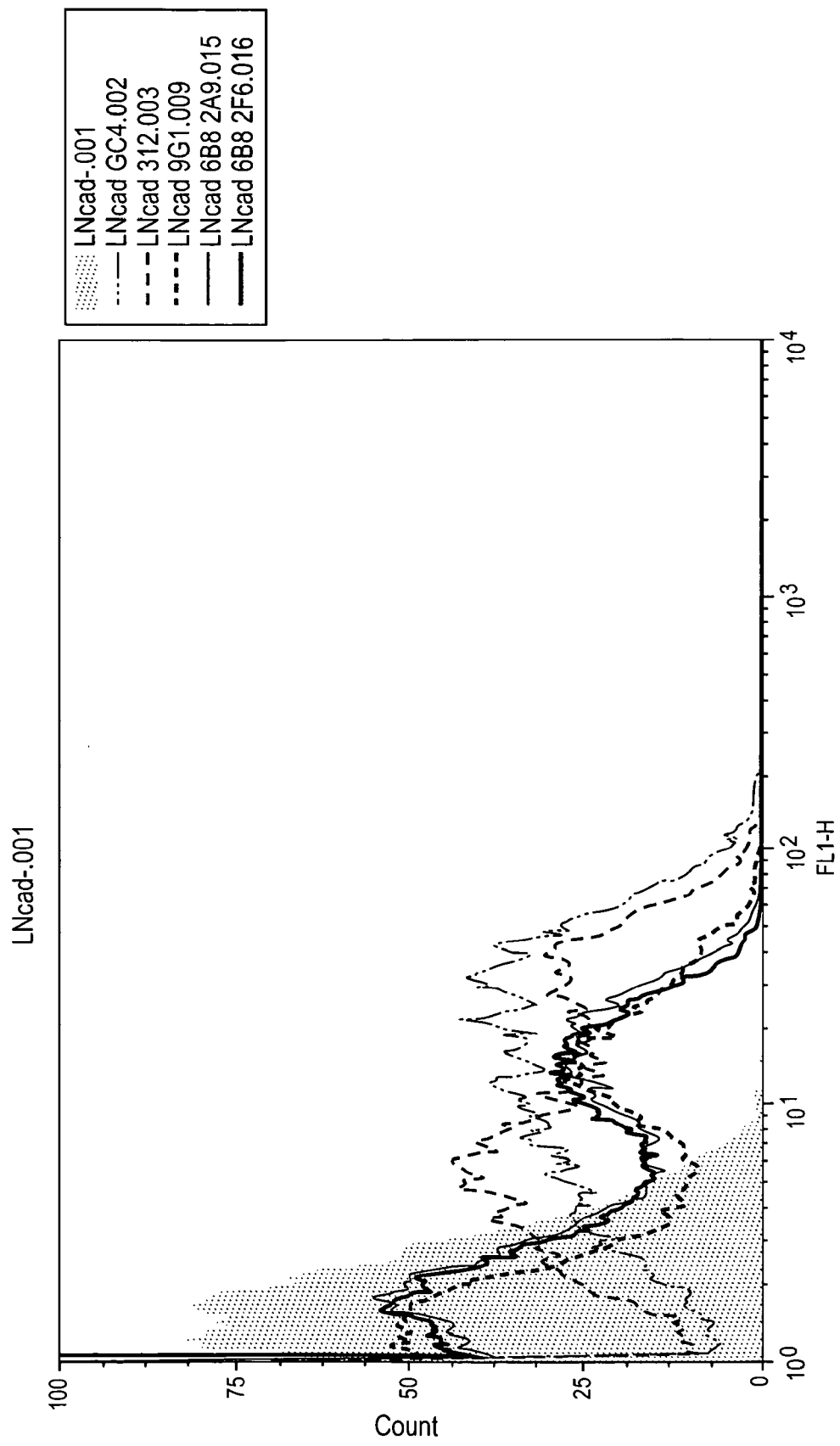
FIG. 14. FACS analysis of antibody clones targeting the fourth extracellular domain of the N-Cadherin protein.

FACS Analysis Showing Screening of Antibody Clones Targeting the Fourth Extracellular Domain of the N-Cadherin Protein FIG. 14 shows that clones recognize N-cadherin on the surface of prostate cancer cells.

Example 11

Subcloning of N-Cadherin Antibodies

Figure 15:
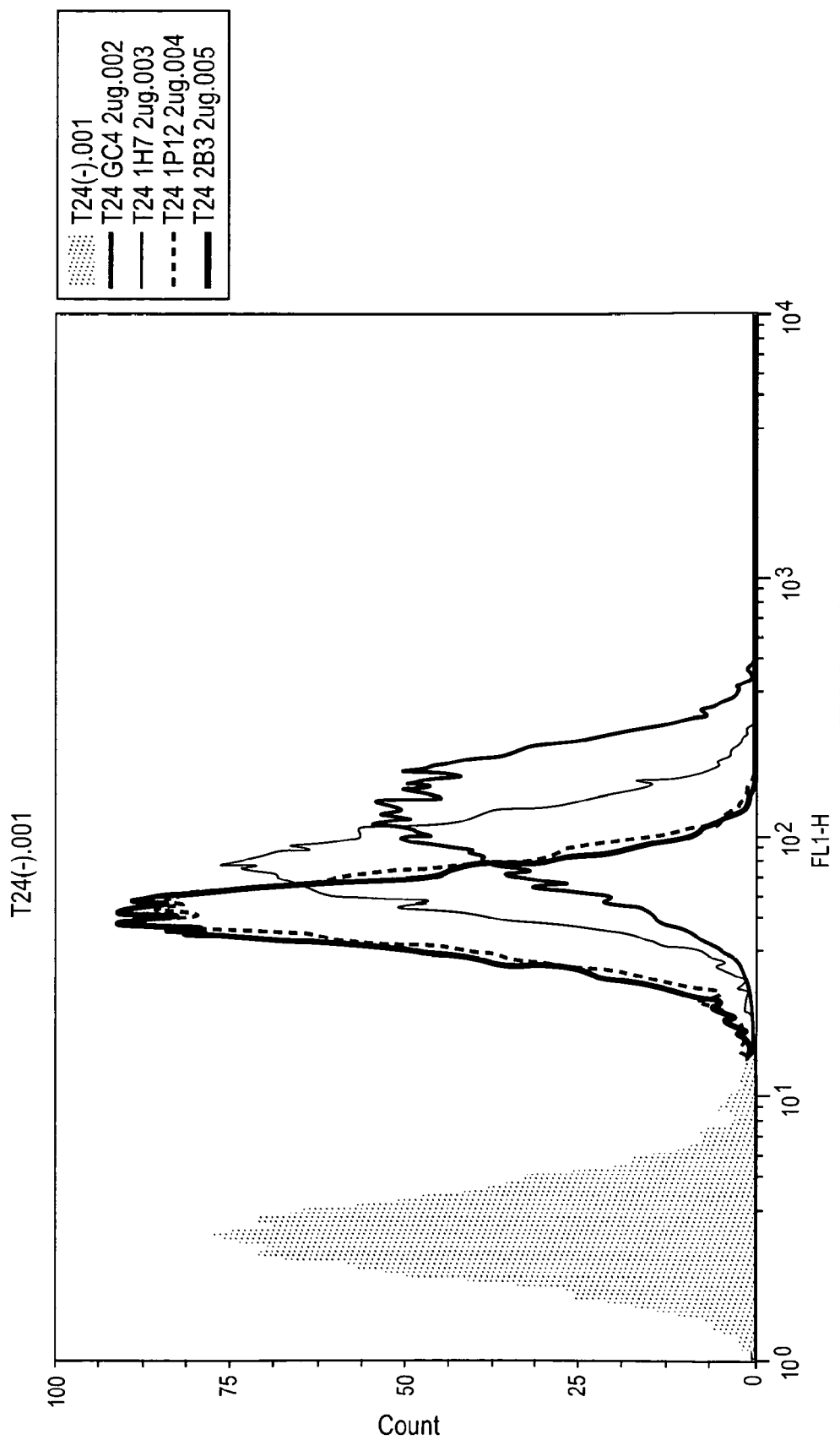
FIG. 15. FACS analysis of purified monoclonal N-Cadherin antibody clones.

FIG. 15 shows that purified monoclonal clones recognize the protein on the cell surface.

Example 12

In Vitro Invasion Assay

Figure 16:
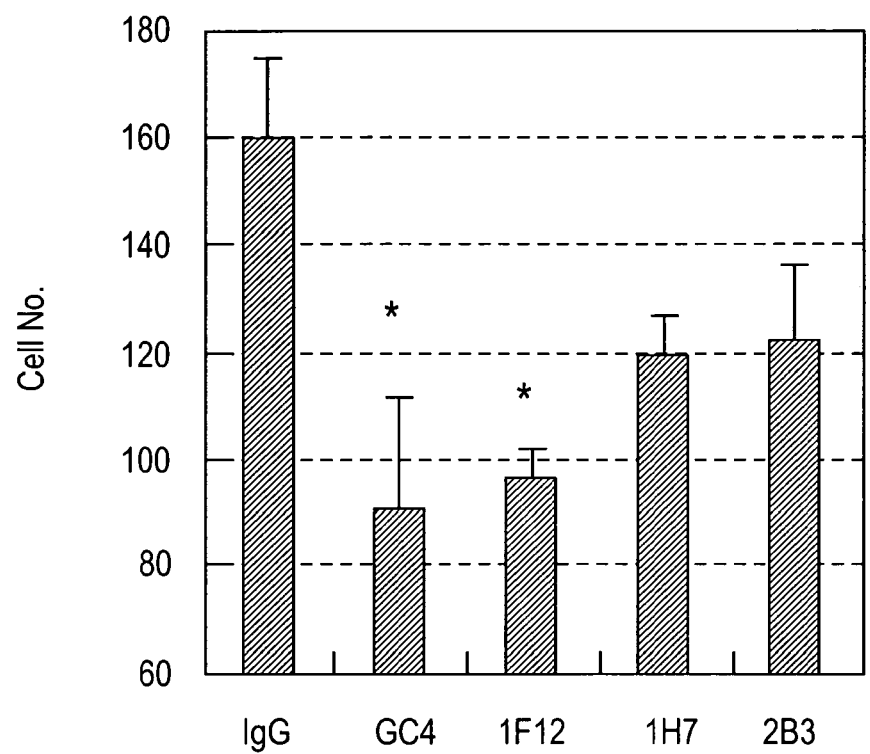
FIG. 16. In vitro invasion assay of monoclonal N-Cadherin antibody clones.

FIG. 16 shows that the monoclonal antibodies 1F12, 1H7 and 2B3 generated by the inventors' group all inhibit the invasiveness of N-cadherin positive cancer cells. GC4 is a control.

Example 13

Figure 17A:
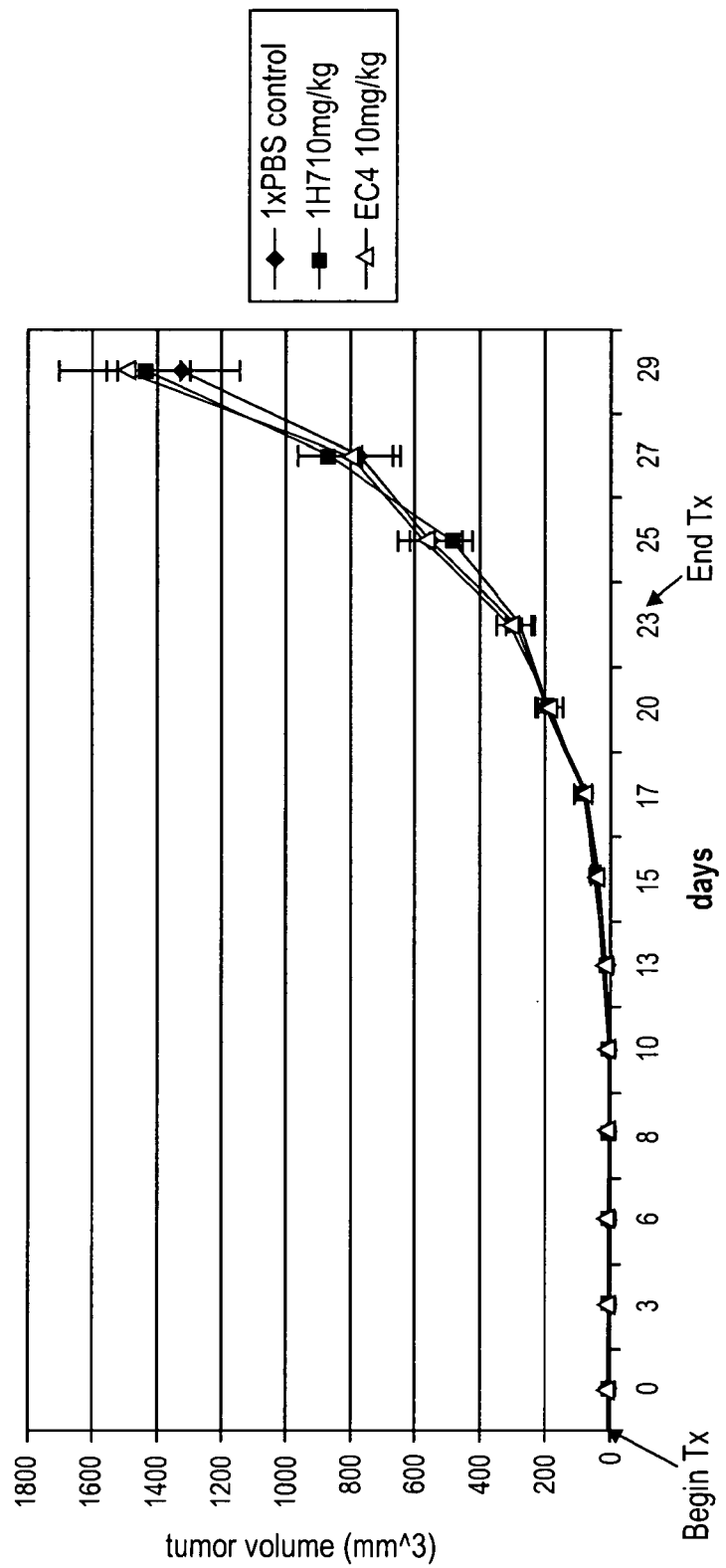
FIG. 17. Growth curve of N-Cadherin null tumors under treatment by antibodies against N-Cadherin, 1H7 and EC4, showing no significant inhibitory effect (17a). Tumor growth curve of PC3 prostate cancer cells treated with the same antibodies, demonstrating effectiveness in growth inhibition (17b). Growth curve of large established PC3 tumors under treatment by the 1H7 and EC4 antibodies (17c). Long term growth curve of PC3 tumors under treatment by the EC4 antibody (17d).
Figure 17B:
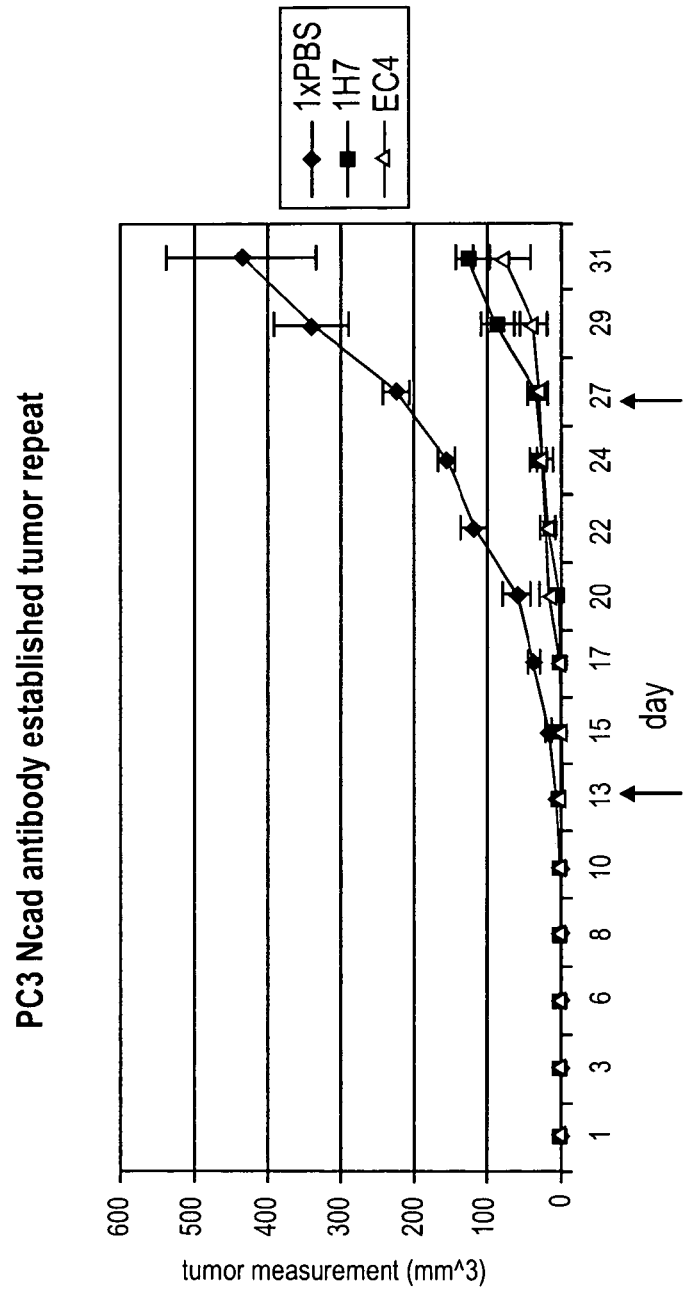
Figure 17C:
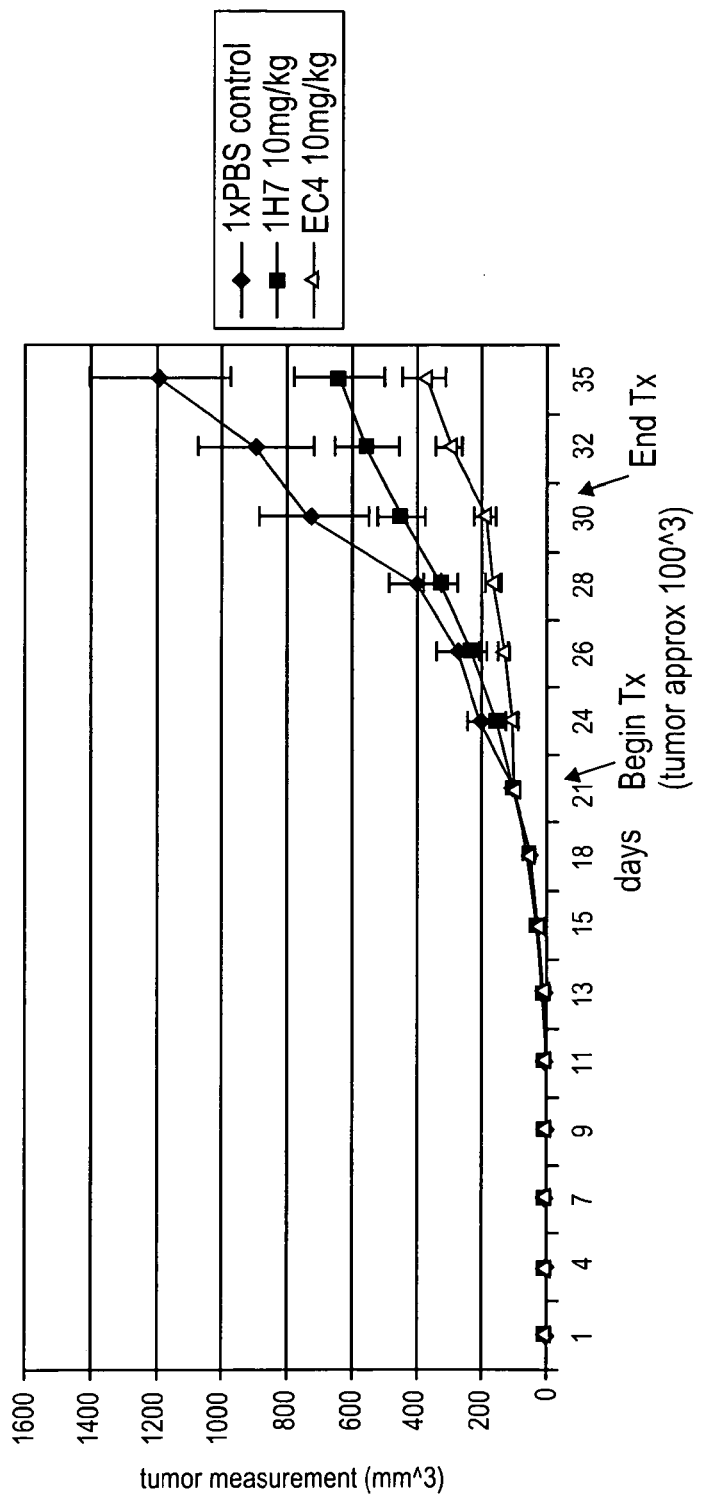
Figure 17D:
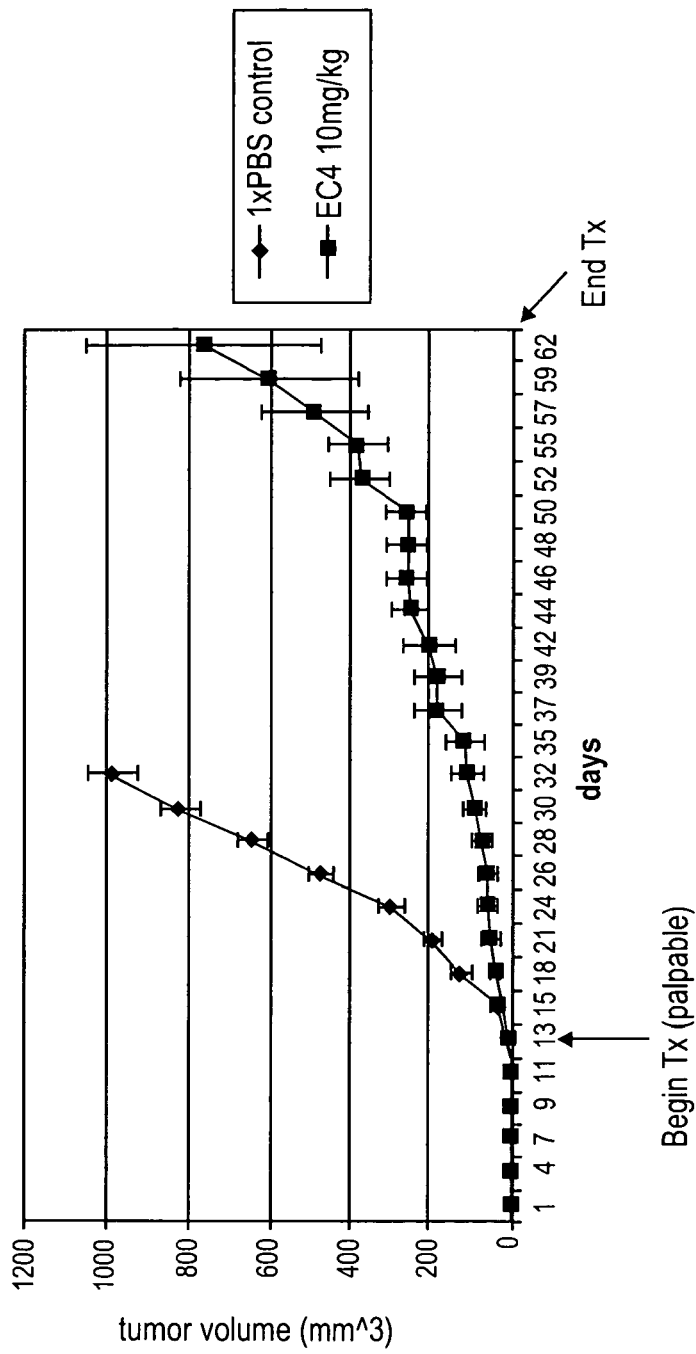

Antibodies against N-Cadherin Block Tumor Growth and Metastasis of PC3 Prostate Cancer Cells, but have No Effect on N-Cadherin Null tumors PC3 cells were implanted subcutaneously and grown. As shown in FIG. 17b, when tumors reached palpable stage at day 15, antibodies or control were given twice weekly (200 micrograms) for two weeks. Both 1H7 and EC4 were able to slow growth of the tumors. They also completely blocked metastasis. 5/5 control mice had lymph node metastases, compared with 0/5 and 0/5 1H7 and EC4 treated mice, respectively. In contrast, the 1H7 and EC4 antibodies had no effect on the growth of N-Cadherin null tumors (FIG. 17a). FIGS. 17c and 17d show clear inhibitory effects of N-Cadherin antibodies on the growth of PC3 tumors, either in treatment of large established tumors (treatment starting on Day 21) or in long term treatment (treatment lasting as long as 62 days).

Example 14

Tumors from In Vivo Experiment Show Affect of Antibodies against N-Cadherin

Figure 18:
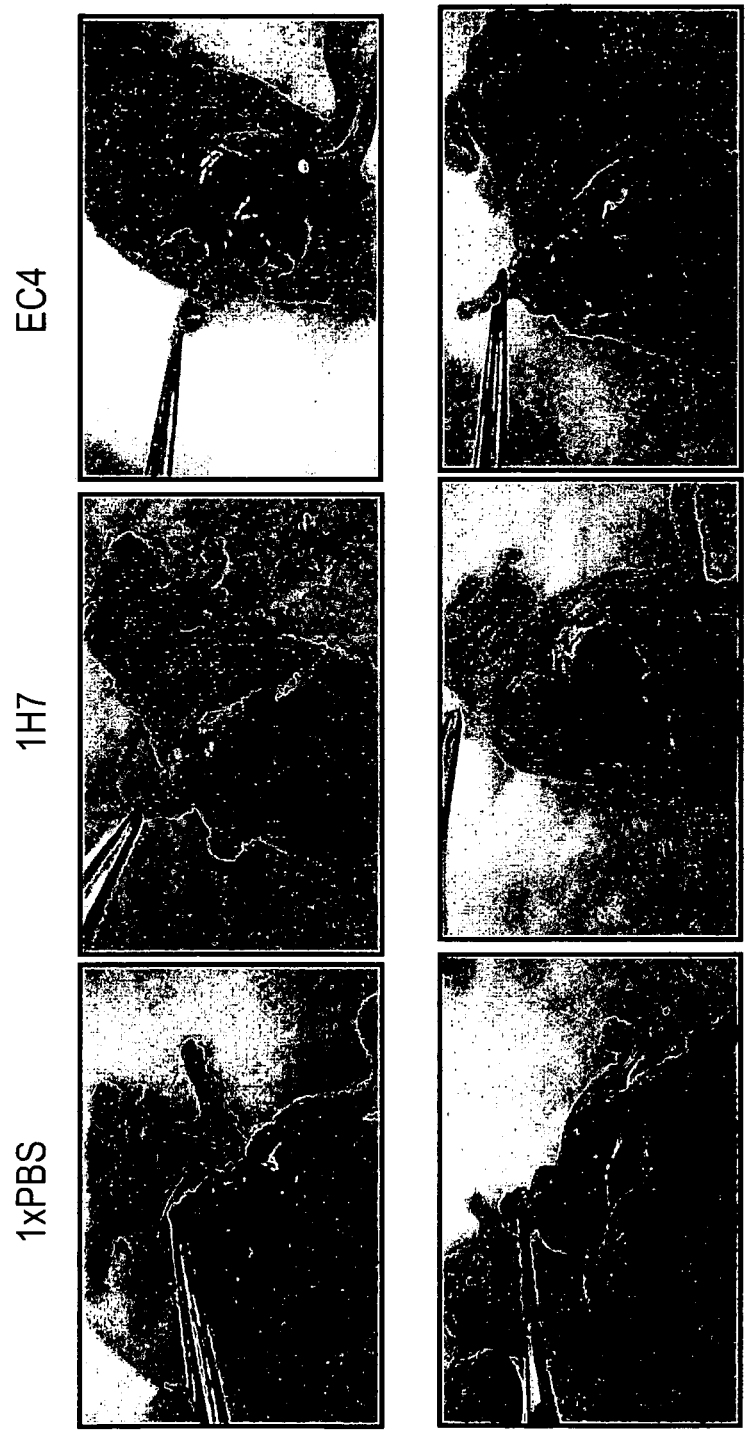
FIG. 18. In vivo experiment showing effect of antibodies against N-Cadherin.

As shown in FIG. 18, the two control tumors are very red consistent with profound angiogenesis. They are also deeply adherent to and invasive into the local flank musculature. In contrast, the 1H7 and EC4 treated mice have pale, clear tumors that do not invade into local muscle. The tumors peel easily off of the underlying tissues, which demonstrates inhibition of angiogenesis and blockade of local invasion by the anti-N-cadherin antibodies, consistent with the finding that these mice had no metastatic disease.

Example 15

Immunohistochemical Staining

Figure 19A:
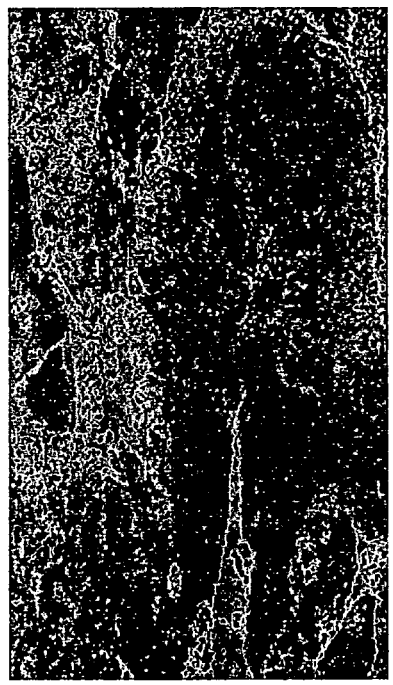
FIG. 19. (a) Immunohistochemical staining of an addrogen independent LAPC9 prostate cancer; (b) Treatment of androgen dependent and independent LAPC-9 tumors with N-cadherin antibodies.
Figure 19B:
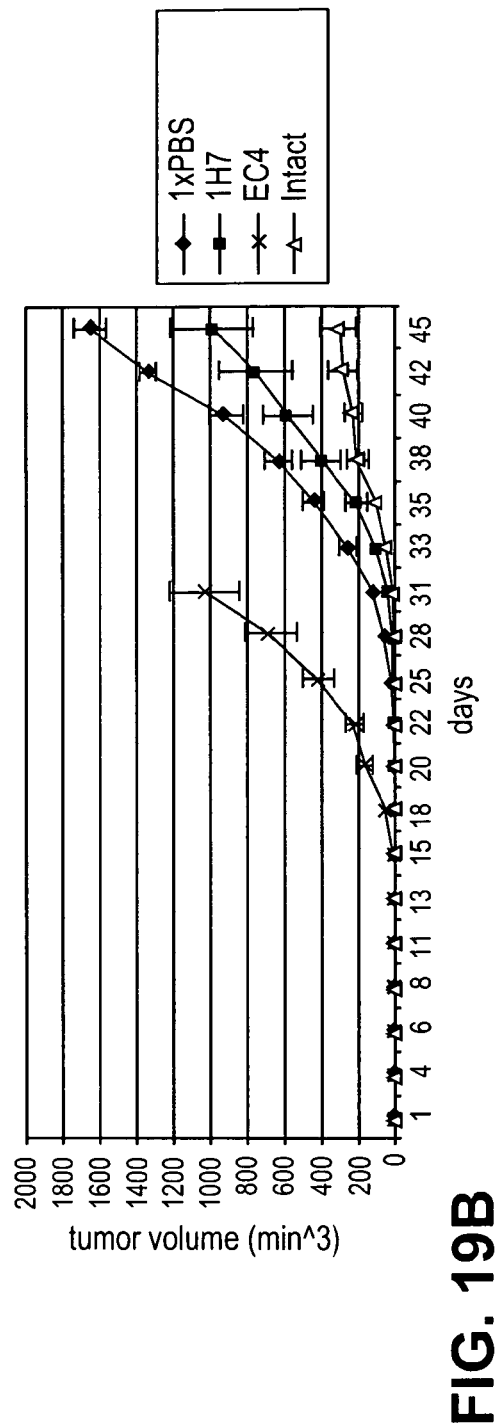

The inventors have carried out immunohistochemical staining of an androgen independent LAPC 9 prostate cancer. The result shows that N-cadherin is only expressed by a small subset of cells (FIG. 19a).

Example 16

Androgen Dependent and Independent LAPC-9 Tumor Growth

Figure 20:
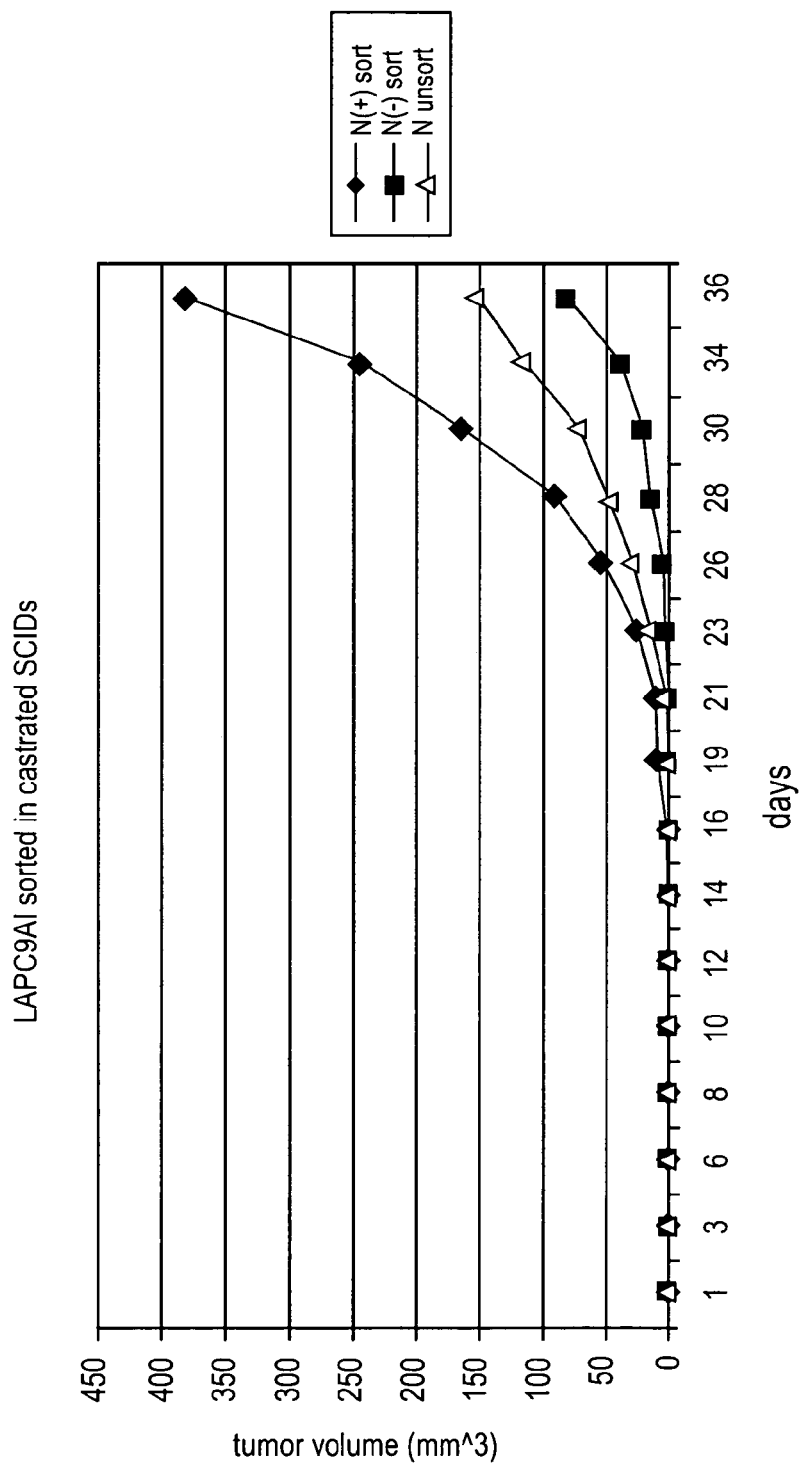
FIG. 20. Tumor Growth Curve of sorted and unsorted LAPC9AI cells.

To determine whether N-cadherin can be a target for treatmet and diagnosis even though N-cadherin is not overexpressed in the cells or only expressed in a subset of cells, the inventors have studied the tumor growth of androgen dependent and independent LAPC-9 tumors. The androgen dependent and independent LAPC-9 tumors were treated with control PBS or N-cadherin antibodies 1H7 and EC4, respectively. The results show that even though N-cadherin is expressed in only a small subset of the androgen independent cells, that treatment with antibody is sufficient to delay the growth and progression of the androgen independent tumors (FIG. 20). These results suggest that the N-cadherin population of cells is required for androgen independent tumor formation, and that blocking it is sufficient to delay tumor progression. These results are consistent with an interpretation that N-cadherin marks a population of androgen independent stem cells. Blocking growth of the stem cells is enough to block growth of the tumor. These results also show that antibodies may work on cells that express normal or even low levels of N-cadherin.

Example 17

Sorted and Unsorted N-cadherin Positive and Negative Tumor Cell Growth

In order to determine the effects of N-cadherin positive cells on tumor cell growth, N-cadherin positive and negative cells were sorted, yielding a population of cells that were 100% and 0% positive for N-cadherin, respectively. Cells were then injected into castrate mice, and the N-cadherin positive cells formed tumors more quickly and efficiently than the negative population (FIG. 20), suggesting that N-cadherin positive cells are either have a growth advantage, or that they have stem cell characteristics and are more tumorigenic than the negative population. Unsorted cells grow similar to the N-cadherin positive cells.

Example 18

FACS Analysis of Tumors from N-Cadherin Sorted Cells

Figure 21:
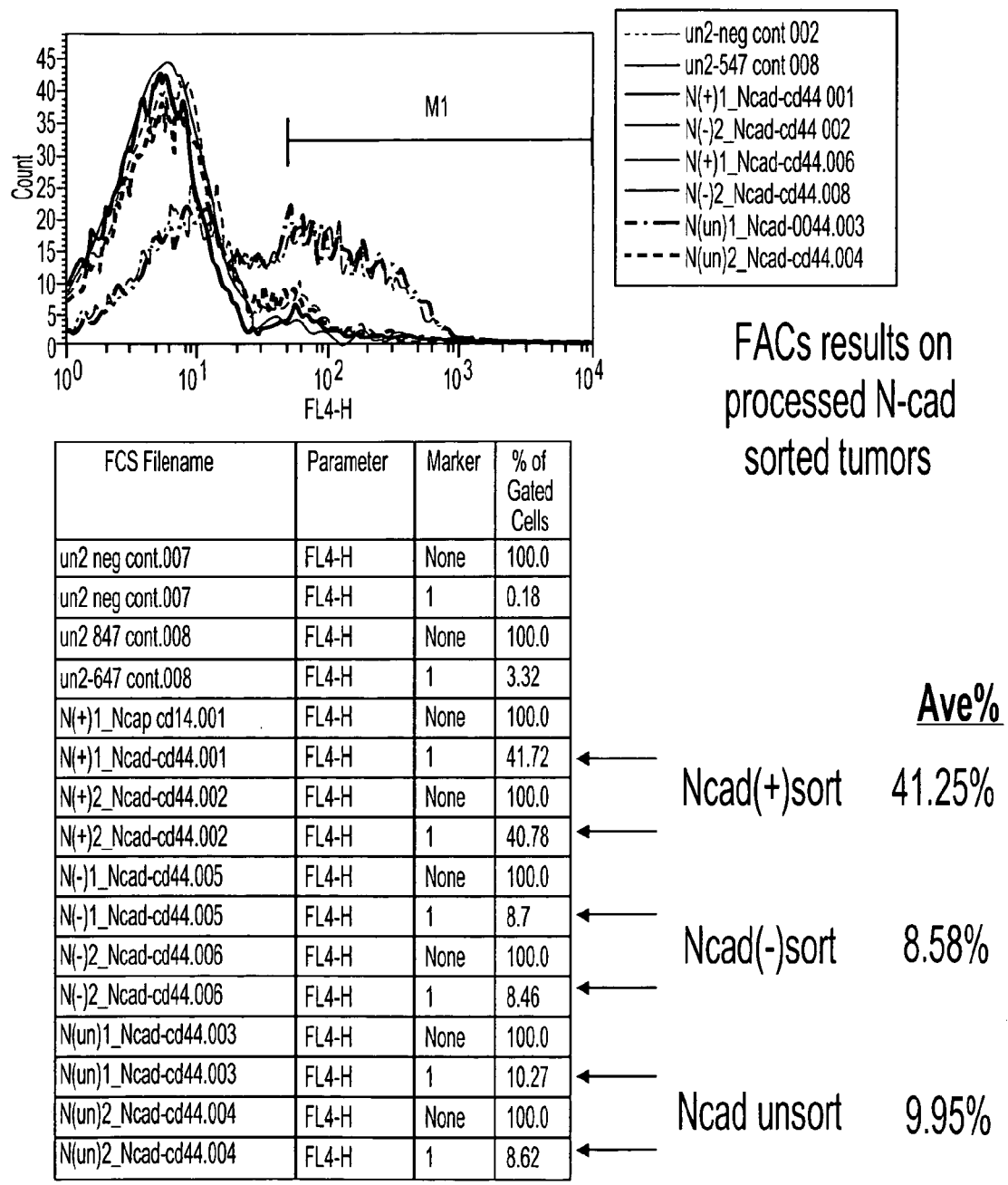
FIGS. 21 and 22. FACS results on processed N-Cadherin sorted tumors.
Figure 22:
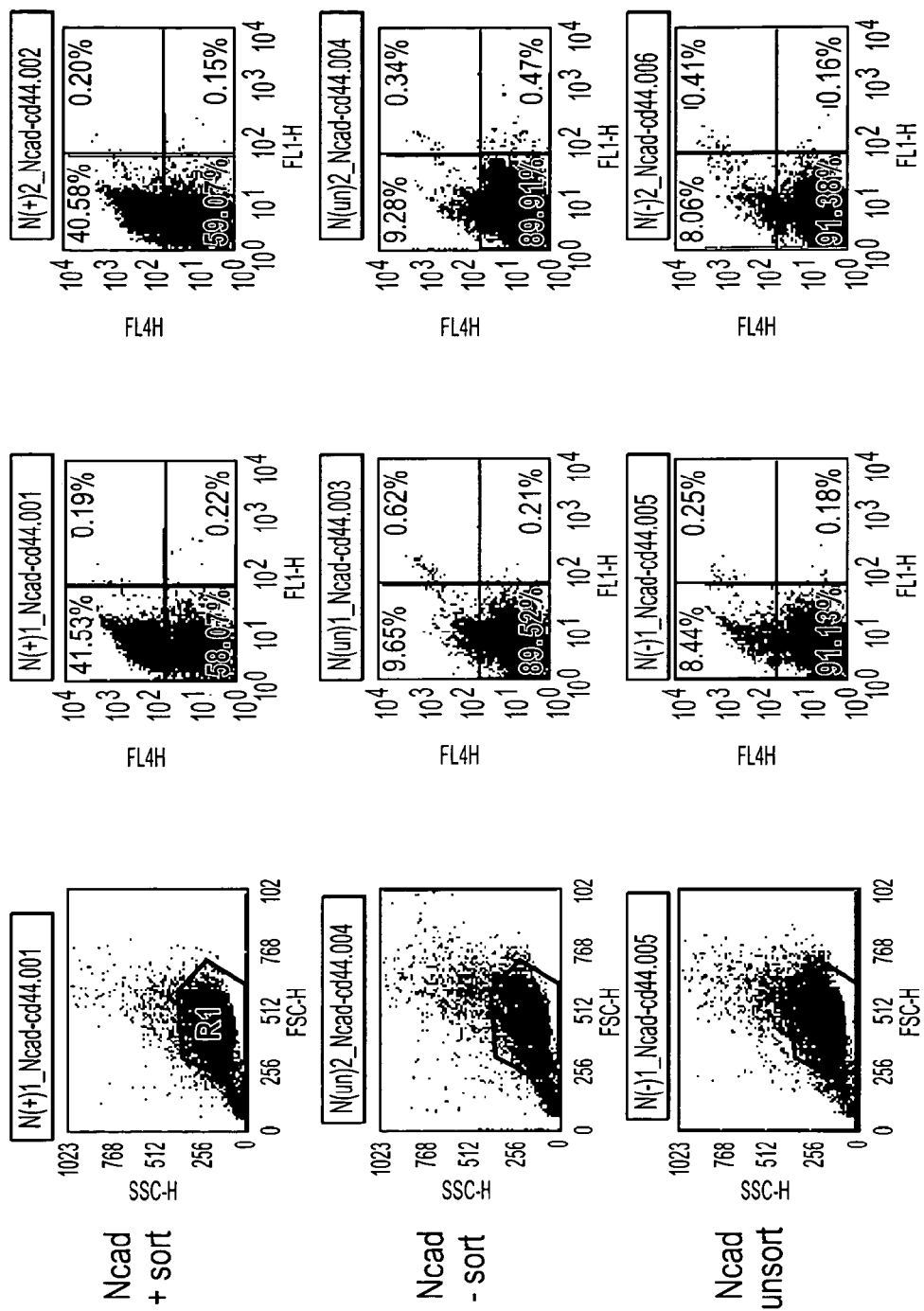

FACS analysis of tumors that grew from purely N-cadherin positive and negative cells, vs the control unsorted population. Tumors from 100% N-cad positive cells are only 41.25% positive for N-cadherin (FIGS. 21 and 22), suggesting that these cells give rise to N-cadherin null cells. This is consistent with the hypothesis that N-cadherin positive cells are stem cells that can give rise to more differentiated, N-cadherin negative cells. Meanwhile, the N-cadherin negative population gives rise to tumors that are 9% N-cadherin positive (FIGS. 21 and 22), similar to the unsorted cells (FIGS. 21 and 22). This suggests that growth of these cells requires that a stem-like population acquire or upregulated N-cadherin in order to form androgen independent tumors. The delay in tumorigenicity is caused by the requirement for N-cadherin to give rise to androgen independent tumors.

Example 19

Growth of Established LNCaP-C1 Tumors are Inhibited by N-Cadherin Antibodies

Figure 23:
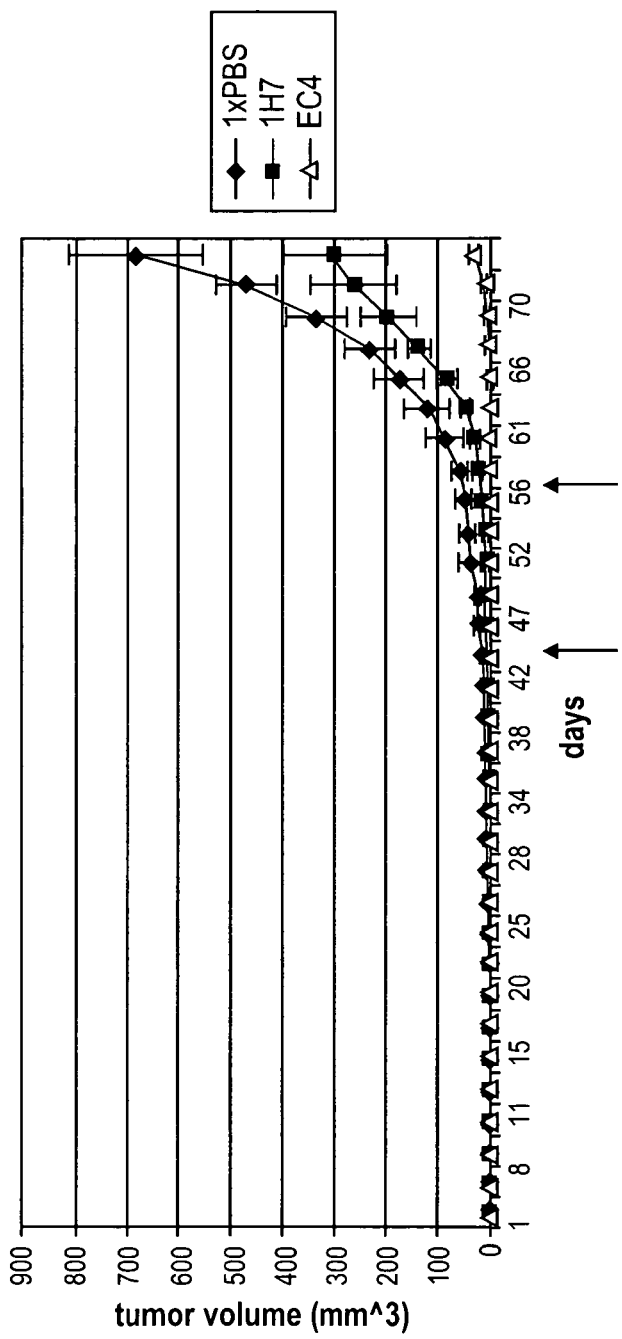
FIG. 23. Growth curves of LNCaP-C1 tumors, showing inhibitory effects of N-cadherin antibodies.

As shown in FIG. 23, N-Cadherin antibodies 1H7 and EC4 were administered to mice bearing LNCaP-C1 tumors from Day 45 to Day 56, and their inhibitory effects on tumor growth were apparent by Day 72.

Example 20

N-Cadherin Antibodies Inhibit Growth of LAPC-9 Androgen Independent Tumors

Figure 24A:
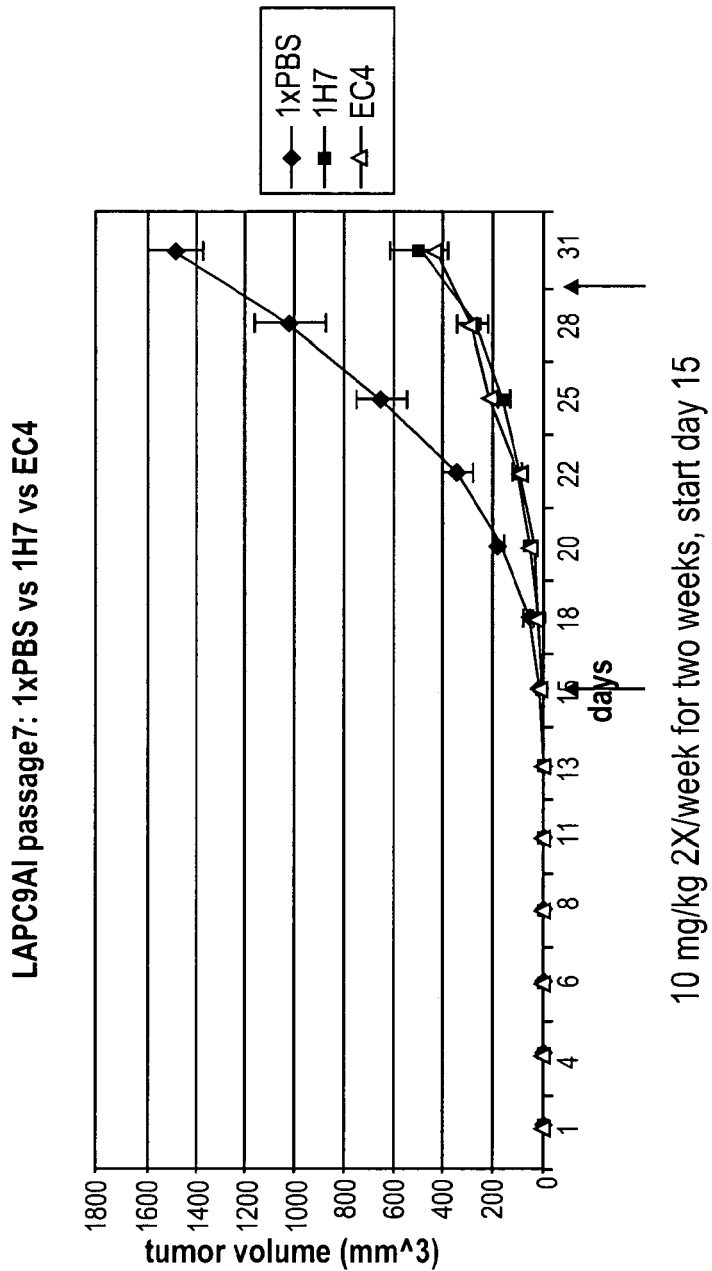
FIG. 24. N-cadherin antibodies inhibit growth of established LAPC-9 androgen independent tumors (24a) and large established LAPC-9 androgen independent tumors.
Figure 24B:
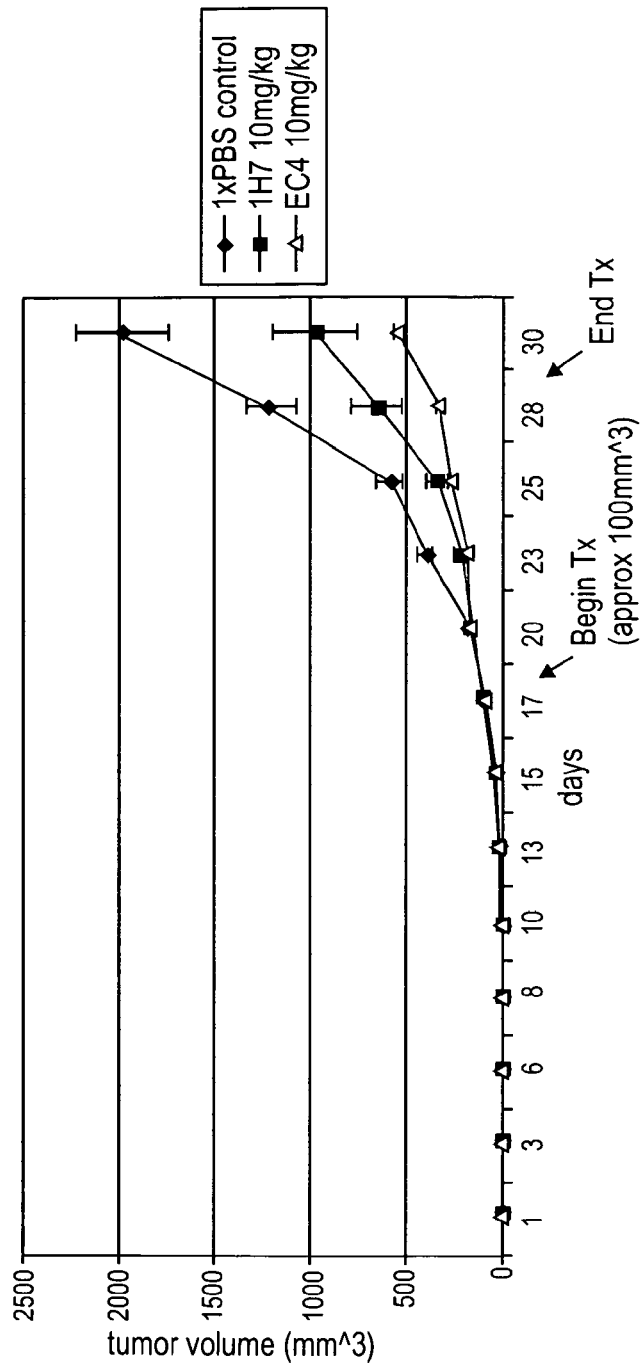

As shown in FIG. 24a, N-Cadherin antibodies 1H7 and EC4 were administered to mice bearing established LAPC-9 androgen independent tumors (passage 7) at 10 mg/kg twice a week starting on Day 15. The inhibitory effect is apparent by Day 30. The inhibitory effects of 1H7 and EC4 on large established LAPC-9 androgen independent tumors are shown in FIG. 24b, where the animals did not receive antibody treatment until Day 17.

Example 21

Does Dependent Growth Inhibition by EC4 Antibody

Figure 25:
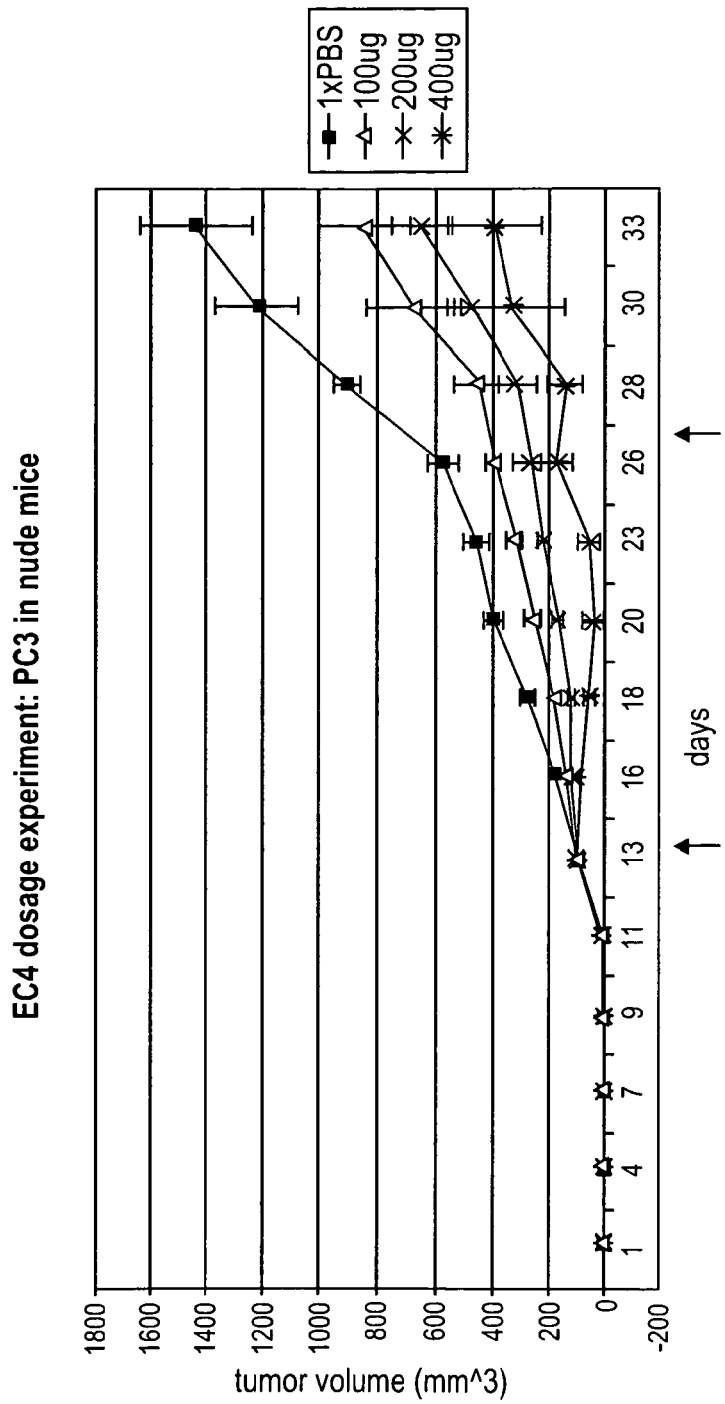
FIG. 25. Inhibition of PC3 tumor growth in nude mice by antibody EC4 in a dose-correlated manner.

As shown in FIG. 25, growth of PC3 tumors in nude mice was inhibited by the EC4 antibody (administered from Day 13 to Day 27), with a more prominent inhibitory effect observed in experiments where a higher dose of the antibody was administered.

Example 22

Toxicity Study

Because N-Cadherin is widely expressed in a variety of tissues, its potential toxicity is a concern if anti-N-Cadherin antibodies are to be used as therapeutic agents. The present inventors have found that the 1H7 and EC4 antibodies cross-react with murine N-Cadherin but no in vivo toxicity has been observed in either long-term or dose escalation studies in mice.

Example 23

Figure 26A:
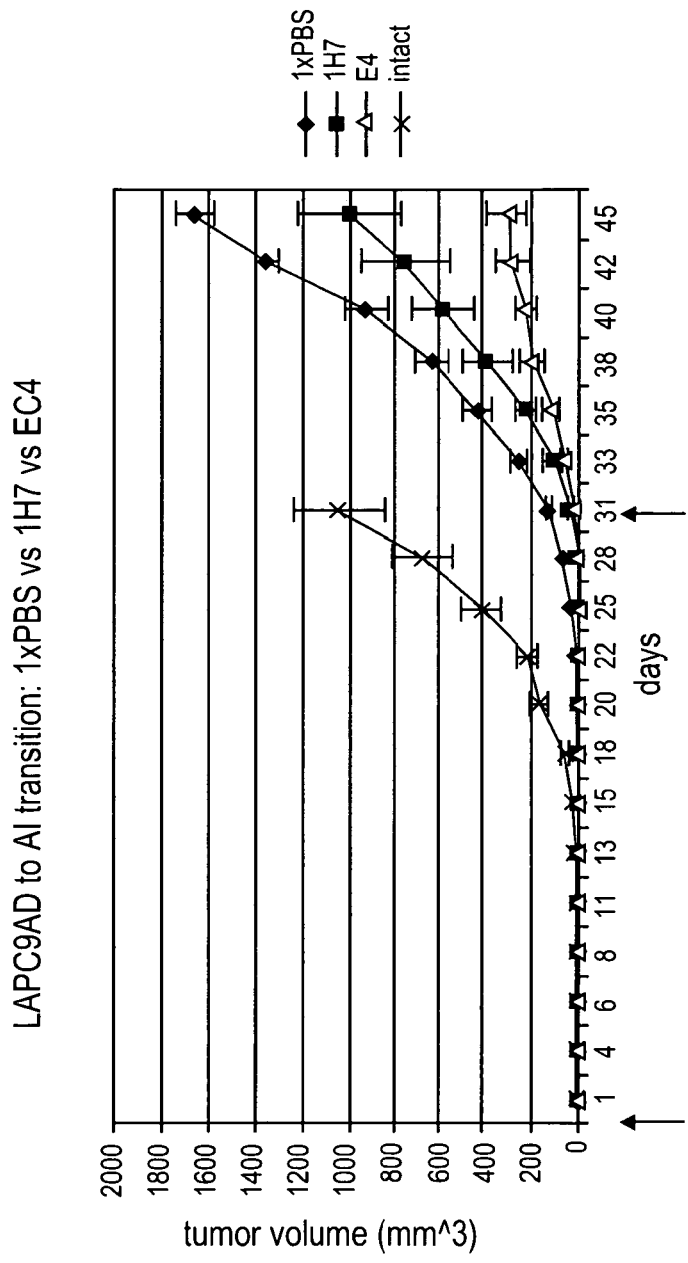
FIG. 26. N-Cadherin antibodies 1H7 and EC4 show an inhibitory effect on the growth of LAPC-9 androgen dependent tumor in two studies in which the tumor pregression was followed for up to 45 days (26a) and 70 days (26b).
Figure 26B:
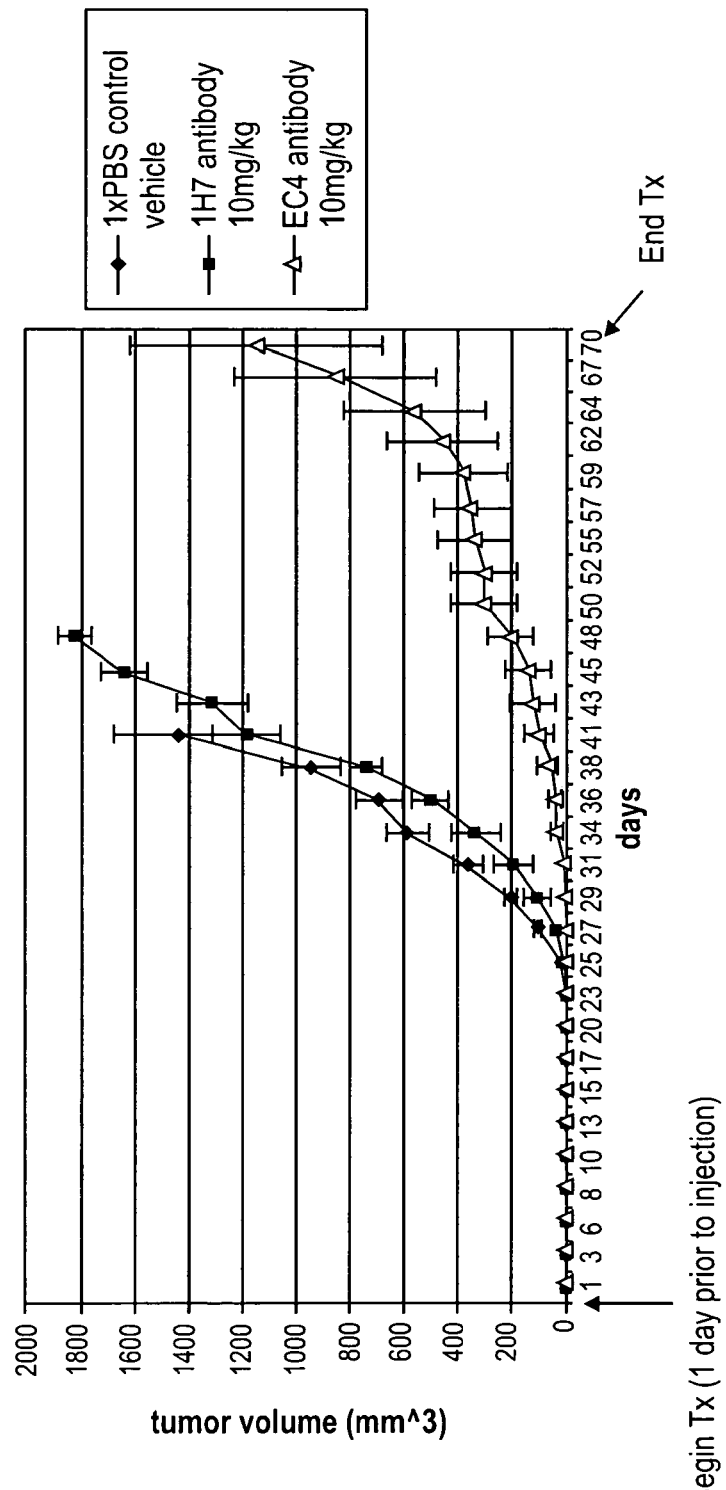

N-Cadherin Antibodies Inhibit Androgen Independent Progression of LAPC-9 Androgen Dependent Tumors As shown in FIGS. 26a and 26b, N-Cadherin antibodies 1H7 and EC4 effectively inhibited the androgen independent progression of LAPC-9 androgen dependent tumors in castrated mice. In the first study (FIG. 26a), the antibodies were administered from Day 0 to Day 31 and the animals were observed for 45 days. In the second study (FIG. 26b), the effect of long term antibody treatment was observed. 1H7 showed moderate delay in tumor progression, whereas EC4 showed a more prolonged effect in blocking tumor progression.

Example 24

N-Cadherin Positive Cells have Growth Advantage in Castrated Mice

Figure 27:
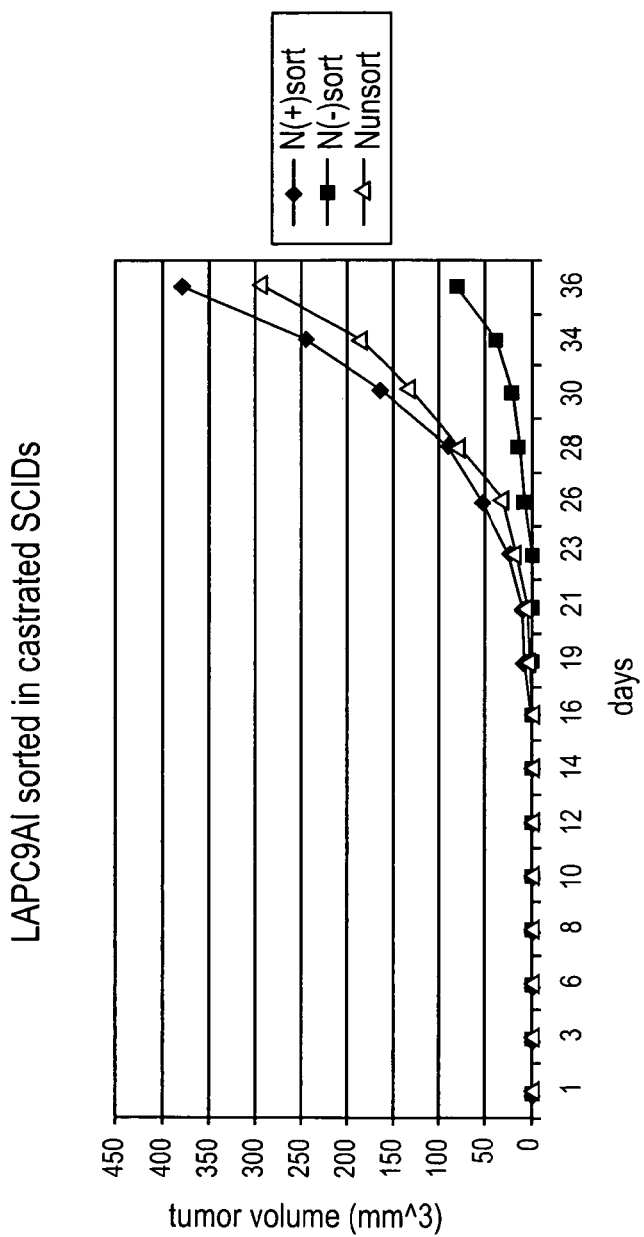
FIG. 27. N-Cadherin sorted cells show a growth advantage in castrated SCID mice.
Figure 28:
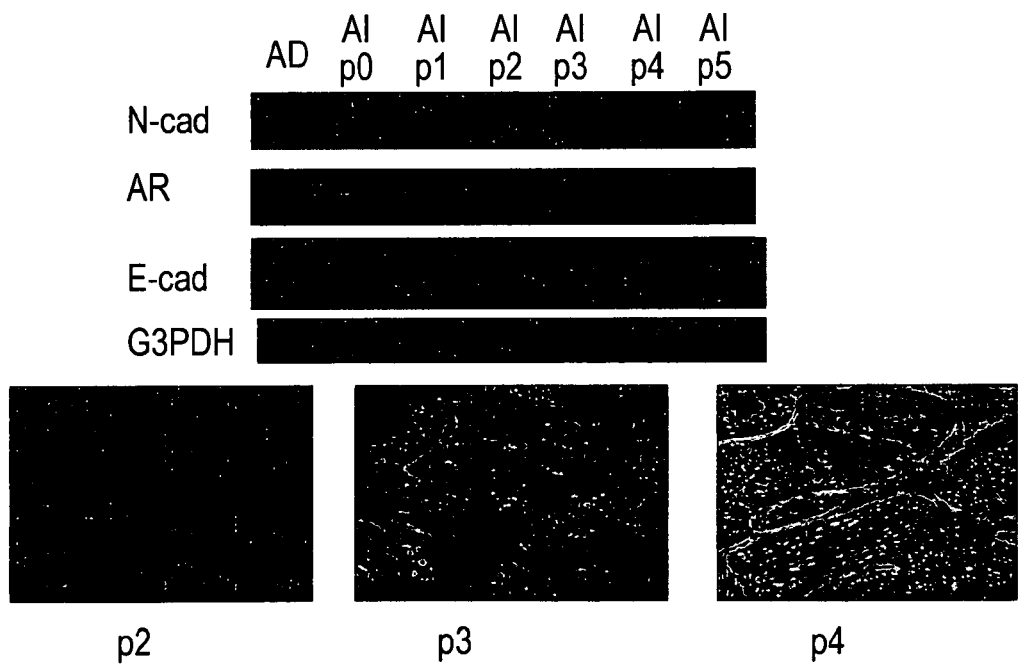
FIG. 28. Correlation between N-cadherin expression and androgen receptor level in successive passages of LAPC9 tumor cells.

As shown in FIG. 27, N-Cadherin positive LAPC-9 tumors showed growth advantage over N-Cadherin negative LAPC-9 tumors in castrated SCID mice. On the other hand, FIG. 28 illustrates the inversed correlation between N-Cadherin expression level and androgen receptor expression in LAPC-9 androgen independent cells: along with the successive passages, the LAPC-9 cells progressly gained androgen independence while their expression of N-Cadherin increased and their expression of androgen receptor decreased.

All patents, patent applications, and other publications, including GenBank Accession Numbers, cited in this application are incorporated by reference in the entirety for all purposes.

What is claimed is:
1. A hybridoma cell line deposited as ATCC Accession No. PTA-9388.
2. An antibody produced by the hybridoma cell line of claim 1.
3. A method of treating a cancer patient with a cancer that expresses a N-cadherin protein, comprising the steps of:
    (a) obtaining a test tissue sample from an individual at risk of having a cancer that expresses a N-cadherin protein;
    (b) determining the presence or absence or amount of the N-cadherin protein in the test tissue sample in compari- son to a control tissue sample from an individual known to be negative for the cancer; thereby diagnosis said cancer the expresses a N-cadherin protein, wherein the N-caderin protein is expressed at normal or low levels, or is expressed by a subset of cells, or is overexpress; and (c) administering an effective amount of the monoclonal antibody of claim 2, or an antigen-binding antibody fragment thereof, to the cancer patient with a cancer that expresses a N-cadherin protein.

4. The method of claim 3, wherein said tissue sample is prostate or bladder tissue.

5. The method of claim 3, wherein said cancer is a prostate cancer.

6. The method of claim 3, wherein said cancer is a bladder cancer.

7. The method of claim 3, wherein said antibody blocks hormone refractory prostate cancer.

8. The method of claim 3, wherein said antibody blocks cancer stem cells.

9. The method of claim 3, wherein said tissue sample is prostate or bladder tissue.

10. The method of claim 3, wherein said cancer is a metastatic cancer.

11. The method of claim 3, where said antibody is the monoclonal antibody of claim 2.

12. The method of claim 3, wherein the antibody fragment is a scFv.

13. The method of claim 3, wherein the antibody fragment is a diabody.

\* \* \* \* \*